United States Patent
Tablan et al.

(10) Patent No.: US 11,990,223 B2
(45) Date of Patent: *May 21, 2024

(54) METHODS, SYSTEMS AND APPARATUS FOR IMPROVED THERAPY DELIVERY AND MONITORING

(71) Applicant: IESO DIGITAL HEALTH LIMITED, Cambridge (GB)

(72) Inventors: Mihai Valentin Tablan, Cambridge (GB); Andrew Blackwell, Cambridge (GB); Ronan Patrick Cummins, Cambridge (GB)

(73) Assignee: IESO DIGITAL HEALTH LIMITED, Cambridge (GB)

( * ) Notice: Subject to any disclaimer, the term of this patent is extended or adjusted under 35 U.S.C. 154(b) by 260 days.

This patent is subject to a terminal disclaimer.

(21) Appl. No.: 17/283,837

(22) PCT Filed: Oct. 10, 2019

(86) PCT No.: PCT/GB2019/052879
§ 371 (c)(1),
(2) Date: Apr. 8, 2021

(87) PCT Pub. No.: WO2020/074903
PCT Pub. Date: Apr. 16, 2020

(65) Prior Publication Data
US 2021/0383913 A1    Dec. 9, 2021

(30) Foreign Application Priority Data

Oct. 10, 2018   (GB) .................................... 1816532

(51) Int. Cl.
*G16H 20/70*   (2018.01)
*G10L 15/26*   (2006.01)
*G16H 50/20*   (2018.01)

(52) U.S. Cl.
CPC ............. *G16H 20/70* (2018.01); *G10L 15/26* (2013.01); *G16H 50/20* (2018.01)

(58) Field of Classification Search
CPC .......... G16H 10/00–80/00; G10L 13/00–99/00
See application file for complete search history.

(56) References Cited

U.S. PATENT DOCUMENTS 10,069,971 B1 *  9/2018  Shaw ................... H04M 3/5133
10,706,873 B2 *  7/2020  Tsiartas ............... G10L 15/1822
(Continued)

FOREIGN PATENT DOCUMENTS

| KR | 20140088327 A | * | 7/2014 |
| WO | 2018158385 A1 | | 9/2018 |
| WO | 2020074903 A1 | | 4/2020 |

OTHER PUBLICATIONS

Wang et al., "Part-of-Speech Tagging with Bidirectional Long Short-Term Memory Recurrent Neural Network," ArXiv, abs/1510.06168. (Year: 2015).*

(Continued)

*Primary Examiner* — Jonathon A. Szumny
(74) *Attorney, Agent, or Firm* — ALSTON & BIRD LLP

(57) ABSTRACT

A computer-implemented method is provided for taking one or more actions relating to therapy, the method comprising: obtaining data comprising audio data relating to a therapy session between a therapist and one or more patients; extracting text data from the audio data to form a transcript; dividing the transcript into a plurality of utterances; using at least a first part of a deep learning model to assign a semantic representation to each of the plurality of utterances to produce a plurality of assigned utterances; compiling the plurality of assigned utterances to form a representation of the therapy session; using at least a second part of a deep learning model, and an input comprising the representation of the therapy session, to obtain an output predicting a (Continued)

characteristic of the therapist, and/or the therapy, and/or the one or more patient; and causing the system to take one or more actions relating to the therapy, wherein the one or more actions are selected based on the output meeting one or more predetermined criterion.

18 Claims, 13 Drawing Sheets

(56) References Cited

U.S. PATENT DOCUMENTS

| | | | |
|---|---|---|---|
| 11,120,895 B2* | 9/2021 | Shriberg | G16H 20/10 |
| 2015/0269857 A1* | 9/2015 | Feng | G09B 7/00 |
| | | | 434/353 |
| 2016/0316059 A1* | 10/2016 | Nuta | G10L 15/04 |
| 2017/0084295 A1 | 3/2017 | Tsiartas | |
| 2017/0354363 A1* | 12/2017 | Quatieri | G10L 25/21 |
| 2018/0150605 A1* | 5/2018 | Co | G10L 15/063 |
| 2018/0214061 A1* | 8/2018 | Knoth | G10L 17/26 |
| 2019/0013092 A1* | 1/2019 | Van Halteren | G09B 19/00 |
| 2019/0121532 A1* | 4/2019 | Strader | G16H 10/20 |
| 2021/0110894 A1* | 4/2021 | Shriberg | G16H 50/50 |
| 2021/0361227 A1* | 11/2021 | Chou | A61B 5/7264 |

OTHER PUBLICATIONS

Cummins et al., "A review of depression and suicide risk assessment using speech analysis," Speech Communication 71 (2015) 10-49; http://dx.doi.org/10.1016/j.specom.2015.03.004. (Year: 2015).*
ISR-WO for PCT/GB2019/052879 dated Dec. 18, 2019.
Olga Davydova, "7 types of Artificial Neural Networks for Natural Language Processing", Sep. 26, 2017 URL:https://medium.com/@datamonsters/artificial-neural-networks-for-natural-language-processing-part-1-64ca9ebfa3b2 p. 8.

* cited by examiner

METHODS, SYSTEMS AND APPARATUS FOR IMPROVED THERAPY DELIVERY AND MONITORING

FIELD OF THE INVENTION

This invention relates to a computer-implemented method for analysing audio data from a spoken interaction between a therapist and a patient. Based on the analysis, a relationship is determined between the contents of a spoken therapy interaction and clinical outcome for the patient, in order that improvements to therapy, and automatic quality assurance of therapy sessions, may be provided. The invention also relates to a system, computer-readable storage medium, and computer program product for carrying out the method.

BACKGROUND OF THE INVENTION

Common mental health disorders including depression and anxiety are characterized by intense emotional distress, which affects social and occupational functioning. About one in four adults worldwide suffer from a mental health problem in any given year. In the US, mental disorders are associated with estimated direct health system costs of $201 billion per year, growing at a rate of 6% per year, faster than the gross domestic product growth rate of 4% per year. Combined with annual loss of earnings of $193 billion, the estimated total mental health cost is at almost $400 billion per year. In the UK mental health disorders are associated with service costs of £22.5 billion per year and annual loss of earnings of £26.1 billion.

Various treatment options for common mental health disorders are available to the clinician; these may include one or more of: watchful waiting, guided self-help, traditional (face-to-face or in-person) cognitive behavioral therapy (CBT) or psychotherapy, CBT delivered over the telephone or similar device, computerised or online CBT, internet-enabled CBT (IECBT), exercise, psychological interventions (brief, standard or complex), medication, social support, combined treatments, and/or electroconvulsive therapy (ECT).

Traditional (face-to-face) psychotherapy and CBT are recognized and widely available treatments for common mental health disorders. The interaction between a therapist and a patient during a therapy session, whether traditional, over the phone, online or internet enabled, is a very important part of the therapy process. Little is known about variation between individual therapy sessions, both in terms of the delivery style and the content of the therapist interaction with the patient, and also how this impacts the quality of the therapy, i.e. the likelihood of a patient improving or recovering.

Compared to the treatment of physical conditions, the average quality of care of mental health disorders remains poor and the rate of improvement in treatment is slow. Outcomes for many mental disorders have stagnated since the original treatments were developed and in some cases the efficacy of psychotherapy appears to be reducing over time. Improving the effectiveness of treatment for any disorder is dependent upon accurate measurement of treatment delivery and an understanding of how the treatment works. Whilst it is relatively simple to monitor and measure the delivery of most medical treatments (e.g. the dosage of a prescribed drug given), monitoring the delivery of psychotherapy (i.e. determining the 'dose' of psychotherapy delivered) is a significantly greater challenge.

For these reasons, a new approach is required to improve, augment or assist with measuring/evaluating the style and content of face-to-face therapy sessions in an unbiased, repeatable manner, leading to improvements in the understanding of key features of good (high quality) therapy sessions, the provision of feedback to therapists, supervisors, therapy services and/or insurance companies, and the provision of improved systems, apparatus, methods and processes for the delivery of therapy.

SUMMARY OF THE INVENTION

According to a first aspect of the present invention there is provided:
a computer-implemented method for taking one or more actions relating to therapy, the method comprising:
obtaining data comprising audio data relating to a therapy session between a therapist and one or more patients;
extracting text data from the audio data to form a transcript;
dividing the transcript into a plurality of utterances;
using at least a first part of a deep learning model to assign a semantic representation to each of the plurality of utterances to produce a plurality of assigned utterances;
compiling the plurality of assigned utterances to form a representation of the therapy session;
using at least a second part of a deep learning model, and an input comprising the representation of the therapy session, to obtain an output predicting a characteristic of the therapist, and/or the therapy, and/or the one or more patient; and
causing the system to take one or more actions relating to the therapy, wherein the one or more actions are selected based on the output meeting one or more predetermined criterion.

In some embodiments, the therapy session may be a face-to-face therapy session.

In some embodiments of the invention each step of the method may be performed in a step-wise manner as set out above, for example first data comprising audio data is obtained, then text data is extracted from that data to form a transcript, then the transcript is divided into utterances, then semantic representations are assigned to the utterances etc. It will be understood by the person skilled in the art that in other embodiments of the invention a number of steps of the method may be performed in any practical order, for example the audio data may be divided into utterances before a text transcript is formed. Alternatively, two or more steps may be conducted contemporaneously.

In one embodiment of the invention, assigning a semantic representation to each of the plurality of utterances may be performed by at least a first part of a deep learning model, and providing an output prediction of one or more characteristic may be performed by at least a second part of the deep learning model. The first and second parts (portions) of the deep learning model may be considered as providing individual functions within one (composite) model (e.g. the therapy insights model). Alternatively, they may be considered as distinct models operating in tandem to provide complementary functions.

The audio data may be separated into two or more audio streams by speaker diarization, each audio stream relating to one of the therapist or the one or more patients. Therefore the system, apparatus or method may be used with just the therapist audio stream, just one patient audio stream, multiple patient audio streams or any combination thereof. This permits independent analysis of the audio streams of any or all of the participants in a therapy session. Suitable methods of speaker diarization will be known to those skilled in the art.

The plurality of utterances may be ascribed to either the therapist or the one or more patient to produce a plurality of therapist utterances and a plurality of patient utterances, thereby a semantic representation may be assigned to each of the plurality of therapist utterances and/or each of the plurality of patient utterances to produce a plurality of assigned utterances. Ascribing individual utterances to either the therapist or the one or more patient may be performed at any suitable point in the method.

Obtaining the audio data may comprise use of a microphone array. A microphone array may comprise a number of microphones arranged within a single device, or a microphone array may comprise a number of microphones in separate devices placed at multiple points in the environment or room in which the therapy session takes place. By using a microphone array a number of audio channels may be inputted, thereby assisting recording and diarization of the audio data.

The data may further comprise video and/or passive data from the therapy session. This data may be collected using the same device on/by which the audio data is collected, or from additional devices. The inclusion of video and/or passive data may permit further data relating to the therapist and/or patient(s) involved in a therapy session to be included in the method, for example facial expression.

The assigned utterances may comprise tagged utterances. Tagging is one example of assigning semantic representations to utterances. Other examples of assigning semantic representations to utterances are known to those skilled in the art.

The input to the second part of the model in accordance with any aspect of the invention may further comprise non-content related session features and/or patient variables. Thereby additional information about a patient, for example gender, age, whether they are taking prescription medication etc., may also be inputted to the method.

The deep learning model may comprise a bidirectional long short-term memory (BiLSTM) neural network or a hierarchical bidirectional long short-term memory (HiBiLSTM) neural network. In other embodiments, the first part of the deep learning model may comprise a bidirectional long short-term memory (BiLSTM) neural network or a hierarchical bidirectional long short-term memory (HiBiLSTM) neural network.

In some embodiments, the output or outputs may comprise:
  a likelihood of clinical improvement by the patient; and/or
  a likelihood of clinical recovery by the patient; and/or
  a likelihood of the patient having a particular mental health disorder; and/or
  a likelihood of engagement by the patient; and/or
  a measure of quality of therapy delivered by the therapist.

In that way, the invention may be used to extract or provide one or more (output) prediction about the therapy, the therapist or the one or more patients, which may be used to improve the provision of the therapy and/or patient outcome.

The output or outputs may be generated in real-time whilst the therapy session is ongoing. The invention may thus provide the possibility of offering real-time (live) evaluation (analysis) of a therapy session and consequent feedback to the therapist and/or their supervisor/employer/healthcare service provider.

Thus real-time (live) analysis and feedback may be provided whilst a given therapy session is ongoing, enabling one or more actions (e.g. advice to the therapist, interventions made by the supervisor etc.) to also be taken whilst the therapy session is live (ongoing). This is expected to increase the quality of the therapy being delivered and improve treatment outcomes for patients.

Alternatively/additionally, the output or outputs may be generated after a particular therapy session or course of therapy sessions has ended.

A measure of quality of therapy delivered by a therapist may be considered to be a measure of the dose of therapy delivered to a patient. By providing an indication of the particular aspects of therapy that are positively correlated with patient improvement, and additionally or alternatively a measurement of the absolute quantity or proportion of those aspects delivered by a therapist, the invention provides an approach to determine the effective dose of therapy delivered.

The one or more action in accordance with any aspect or embodiment of the invention may comprise, in response to the representation meeting a predetermined criterion, initiating an automated therapist support process that comprises providing information to the therapist via the system. Thereby the therapist may be directed to improve the therapy they are delivering. The direction provided to the therapist may comprise a recommendation to either increase or decrease the number or frequency of utterances belonging to one or more categories, in order to improve the quality of the therapy and therefore clinical outcome. Where the therapy is provided partially or wholly by a computer-based system, the direction may be provided to the therapist by that system.

Alternatively/additionally, the one or more action in accordance with any aspect or embodiment of the invention may comprise, in response to the representation meeting a predetermined criterion, initiating an automated quality assurance process that comprises alerting a supervisor, service or payer of the therapist to below-average quality therapy delivery by the therapist. Alternatively/additionally, the one or more actions may comprise, in response to the output or output prediction meeting a predetermined criterion, initiating an automated therapy quality assurance process that comprises alerting a supervisor, service or payer of the therapist to below-average quality therapy delivery by the therapist. Alerting a supervisor may comprise recommending one or more further action. The one or more further action would suitably be selected to be appropriate to the criterion met by the output or output prediction, and would be designed to improve the patient outcome by improving the provision of therapy, either by increasing the quality of therapy provided by the existing therapist, or by reallocating the patient to a different (more experienced) therapist. Automated QA provides benefits over conventional QA methods (e.g. manual tagging of therapy session utterances by experienced therapists). Automated QA is expected to perform more consistently than human tagging/analysis, where individual taggers may differ in their opinion. Furthermore, the cost of therapy QA provision by experienced therapists (both financial and in terms of allocation of time of experienced therapists) is much greater than the cost of therapy QA provision by the invention. Therefore therapy QA provision by the invention permits more therapy sessions (suitably all therapy sessions) to be analysed in a cost effective manner, reducing the cost of therapy and allowing the attention of experienced therapists (supervisors) to be focused where it is most beneficial.

Alternatively/additionally, the one or more action in accordance with any aspect or embodiment of the invention may comprise, in response to the representation meeting a predetermined criterion, initiating an automated therapy auditing process that comprises collecting a plurality of outputs of the method relating to one or more therapy sessions or one or more therapists. Alternatively/additionally, the one or more action in accordance with any aspect or embodiment of the invention may comprise, in response to the output or output prediction meeting a predetermined criterion, initiating an automated therapy auditing process that comprises collecting a plurality of outputs of the method relating to one or more therapy sessions or one or more therapists.

Alternatively/additionally, the one or more action in accordance with any aspect or embodiment of the invention may comprise, in response to the representation meeting a predetermined criterion, initiating an automated output report to one or more of: the therapist, a supervisor of the therapist, a service to which the therapist belongs and the payer for the therapy. Alternatively/additionally, the one or more action in accordance with any aspect or embodiment of the invention may comprise, in response to the output meeting a predetermined criterion, initiating an automated output report to one or more of: the therapist, a supervisor of the therapist, a service to which the therapist belongs and the payer for the therapy.

Alternatively/additionally, the one or more action in accordance with any aspect or embodiment of the invention may comprise, in response to the representation meeting a predetermined criterion, initiating an automated medical diagnosis process that comprises providing a prediction of the presence of a mental health disorder in the one or more patient. Alternatively/additionally, the one or more action in accordance with any aspect or embodiment of the invention may comprise, in response to the output meeting a predetermined criterion, initiating an automated medical diagnosis process that comprises providing a prediction of the presence of a mental health disorder in the one or more patient.

Alternatively/additionally, the one or more action in accordance with any aspect or embodiment of the invention may comprise, in response to the representation meeting one or more predetermined criterion, initiating an automated data collection process that comprises storing one or more of: the audio data, the audio streams, the transcript, the utterances, the assigned utterances, and/or the representation. Alternatively/additionally, the one or more action in accordance with any aspect or embodiment of the invention may comprise, in response to the output meeting a predetermined criterion, initiating an automated data collection process that comprises storing the audio data, the audio streams, the transcript, the utterances, the assigned utterances, and/or the representation.

In accordance with any aspect of the invention, the one or more action in accordance with any aspect or embodiment of the invention relating to the therapy may be taken in real-time whilst the therapy session is ongoing. Thereby improvements to the therapy session may be made as soon as they are indicated by the system.

The audio data, the audio streams and/or the transcript may be provided to one or more of: the patient, the therapist, the supervisor of the therapist, the service to which the therapist belongs and the payer for the therapy.

The therapy may comprise psychotherapy. In some embodiments, the therapy may comprise a talking therapy, or coaching. In some embodiments the therapy may comprise cognitive behavioural therapy (CBT), online CBT or internet-enabled CBT. The patient may have a mental health disorder. Having a mental health disorder (i.e. a psychological condition), or a particular example of such, means a patient is referred to the therapist/therapy service, or self-refers to the therapist/therapy service, because the patient presents with/exhibits one or more symptoms of a mental health disorder, resulting in the presence of a mental health disorder in that patient being suspected. Alternatively or additionally, the patient may have been diagnosed with a mental health disorder using standard diagnostic measures/techniques. Alternatively, a patient may have been predicted to have a mental health disorder, or a psychological condition, or a particular example of such, by a suitable computer-implemented method.

In some embodiments in accordance with any aspect of the invention, the mental health disorder may be selected from an adjustment disorder, agoraphobia (with or without panic disorder), unspecified anxiety disorder, chronic fatigue syndrome, chronic intractable pain, depressive episode, dysthymia, an eating disorder, generalised anxiety disorder, hypochondriacal disorder, mental and behavioural disorders due to use of alcohol, obsessive-compulsive disorder, panic disorder (episodic paroxysmal anxiety), post-traumatic stress disorder (PTSD), recurrent depressive disorder, sexual dysfunction, a sleep disorder, social phobias and/or somatoform disorders. In some embodiments in accordance with any aspect of the invention, the mental health disorder may be selected from depression or an anxiety disorder. Other suitable disorders will be known to those skilled in the art. In some embodiments, the patient may have a mental health disorder; the mental health disorder may comprise for example depression, an anxiety disorder, PTSD, an eating disorder, a sleep disorder or sexual dysfunction.

According to a further aspect of the present invention there is provided a computer program product comprising instructions which, when the program is executed by a processor, cause the processor to carry out a method according to any aspect of the invention.

According to a further aspect of the present invention there is provided a non-transitory computer-readable medium comprising instructions which, when executed by a processor, cause the processor to carry out the method according to any aspect of the invention.

According to a further aspect of the present invention there is provided a data processing system for carrying out the method according to any aspect of the invention, the system comprising: a processor; a natural language processing unit; and a memory unit.

According to another aspect of the invention there is provided a method of treating of a mental health disorder in a patient comprising use of a computer program product, a non-transitory computer-readable medium, or a data processing system in accordance with any aspect of the invention.

According to another aspect of the invention there is provided a method of treating a patient with a computer program product in accordance with any aspect of the invention, a non-transitory computer-readable medium in accordance with any aspect of the invention, or a data processing system in accordance with any aspect of the invention, wherein the patient has a mental health disorder.

According to another aspect of the invention there is provided a computer program product, a non-transitory computer-readable medium, or a data processing system in accordance with any aspect of the invention for use in the treatment of a health disorder or condition, such as a mental health disorder, e.g. depression or anxiety.

Improving quality of care of mental health disorders and improving the efficacy of psychotherapy requires that treatment be delivered as intended, however monitoring and quantifying the delivery of psychotherapy was heretofore a substantial challenge.

The systems and methods of the invention may therefore be used to improve the quality of therapy delivered to patients, and thereby improve patient outcome (likelihood of improvement or recovery). The invention may also be used to improve and refine the therapy delivered to particular patient groups, thereby providing differentiated healthcare (personalised medicine). By improving and refining the therapy delivered, patients may be more likely to improve and/or recover, and may require fewer sessions of therapy. This is beneficial to the patient in terms of time, convenience, cost (both of monetary cost of therapy, and also reduced cost from e.g. time off work), and is also beneficial to the therapist or healthcare service in terms of increasing the numbers of patients treatable in a given time, reducing overheads per patient, and increasing profit in a pay-for-value payment model.

The systems, devices and methods described herein represent a new approach for quality controlled behavioral health care. For example, the approach described herein provides a method of monitoring therapists' performance. 'Therapist drift'—the failure to deliver treatments that a therapist has been trained to deliver—is considered one of the biggest factors contributing to poor delivery of evidence based treatment (G. Waller, Evidence-based treatment and therapist drift. Behav. Res. Ther. 47, 119-127 (2009)). Automated monitoring of therapists' performance could help prevent therapist drift and associated lower improvement rate, phenomena that have been particularly noted in the case of more experienced therapists. The approach described herein could be applied to monitor and inform the practice of face-to-face psychotherapy.

A major factor thought to underlie therapist drift is the increase in the confidence a therapist develops over time in their own knowledge above that of therapeutic guidelines (G. Waller, H. Turner, Therapist drift redux: Why well-meaning clinicians fail to deliver evidence-based therapy, and how to get back on track. Behav. Res. Ther. (2016), doi:10.1016/j.brat.2015.12.005). The aspects of the invention described herein provide valuable improvements over traditional therapy, therapy monitoring and consequent actions, for example by reducing the incidence of therapist drift.

DETAILED DESCRIPTION OF THE INVENTION

The invention relates to computer-implemented methods, apparatus and systems that provide insights into the content of a face-to-face therapy session, and uses of those aspects in the treatment of mental health disorders. The insights thus gained are turned into actions that include: the automated output of information to the therapist; making recommendations to the therapist; providing automated, unbiased quality assurance and auditing of therapy sessions, and identifying correlations between patient characteristics, contents of spoken or face-to-face therapy interactions and (clinical) outcomes for the patients.

FIGURES

Figure 1:
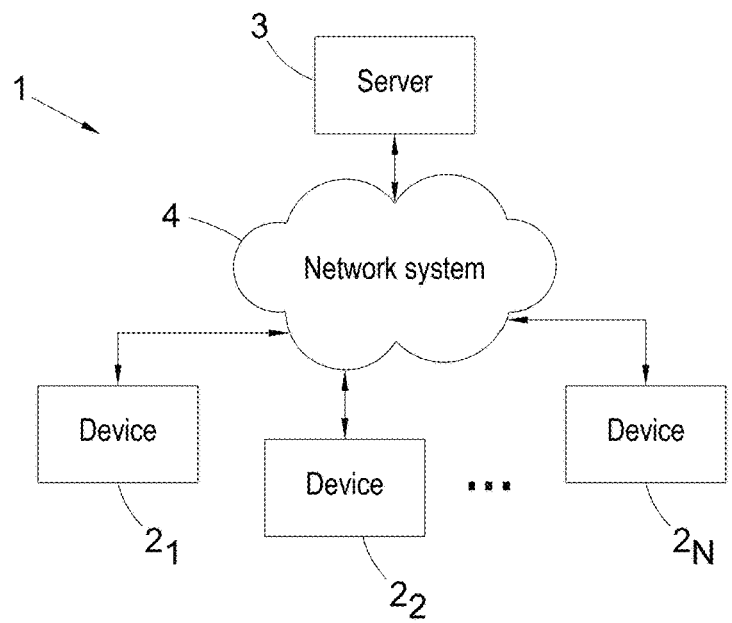
FIG. 1 illustrates an exemplary system for providing therapy.
Figure 3:
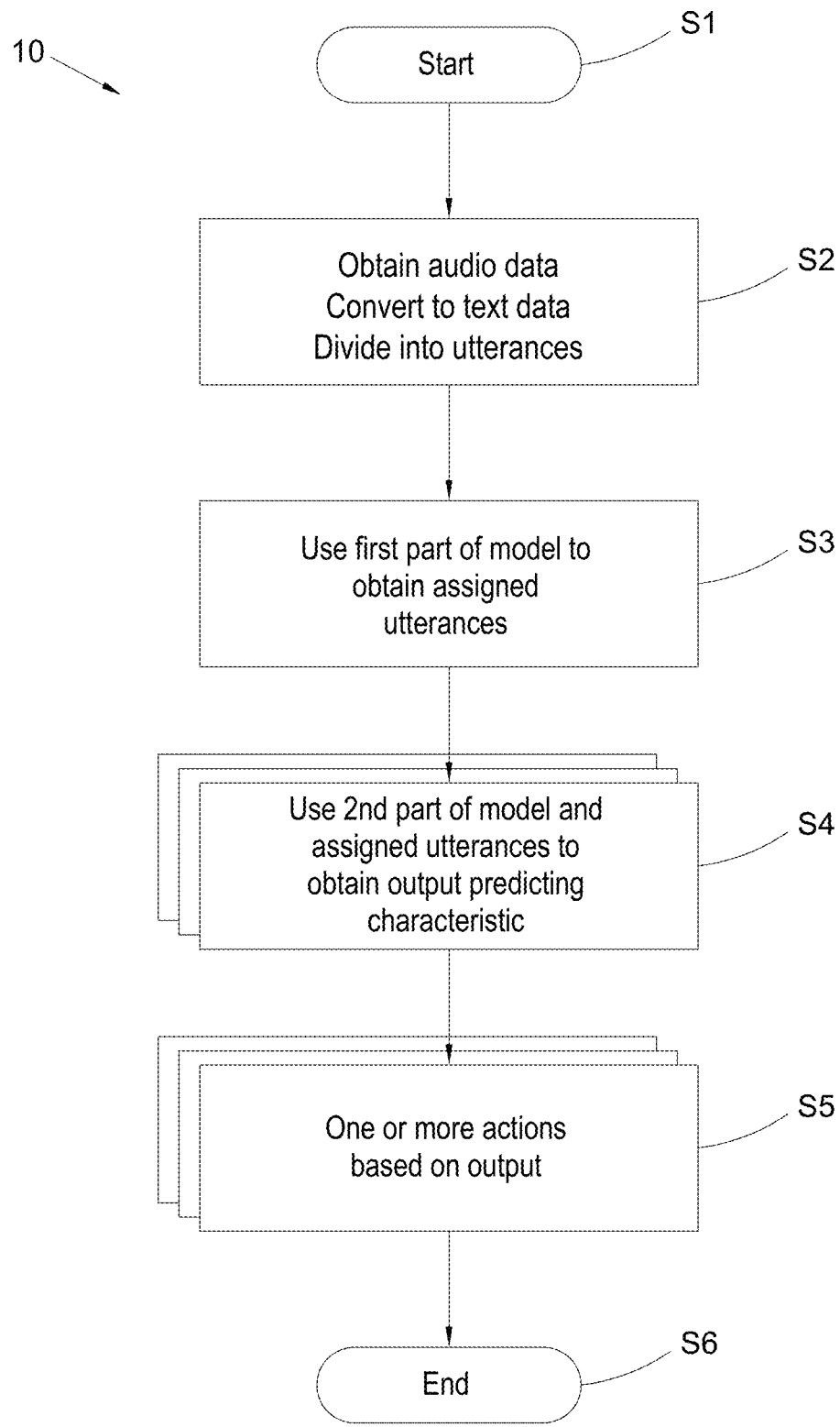
FIG. 3 illustrates a method which may be carried out by the system of FIG. 1.
Figure 4:
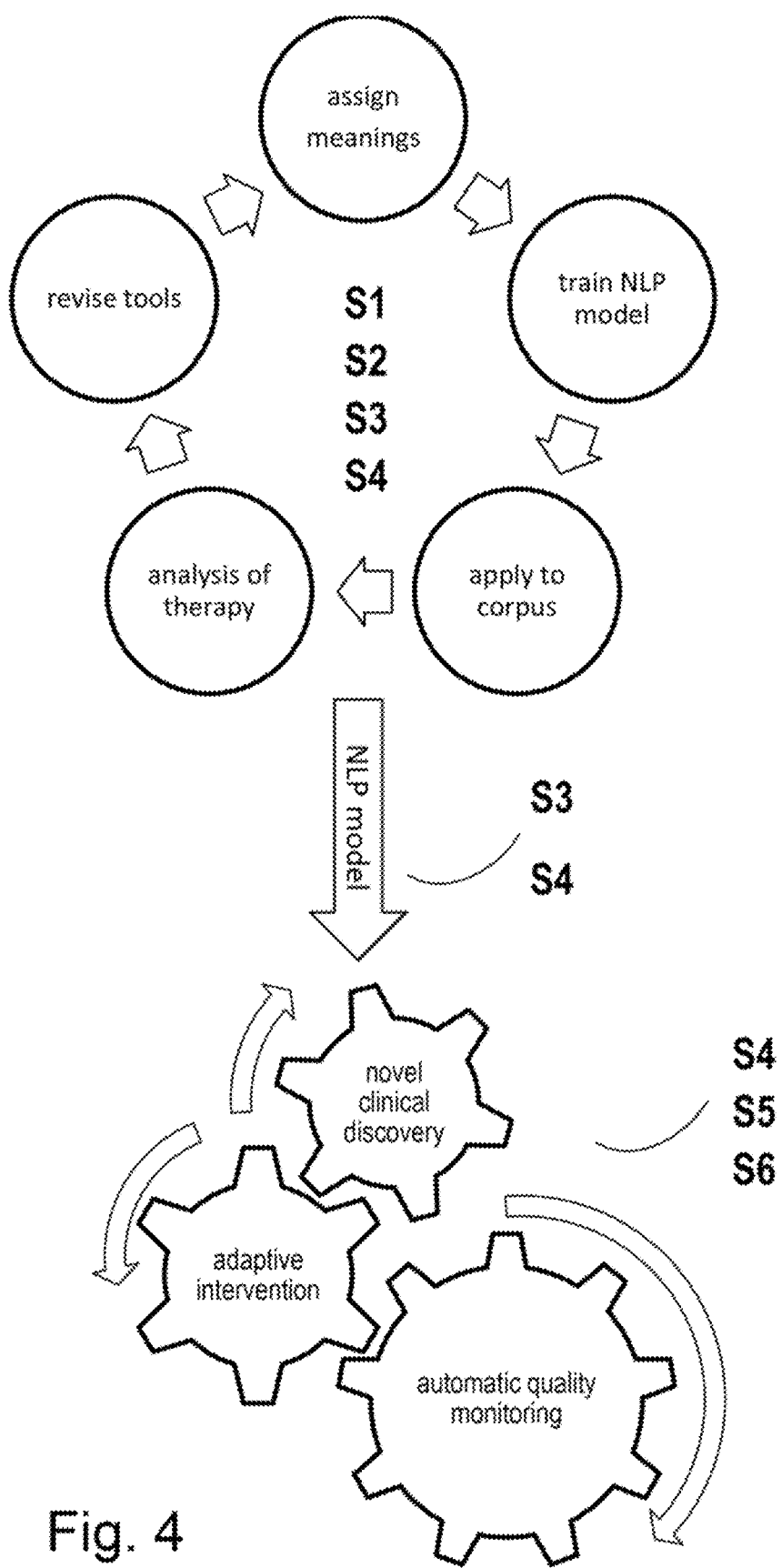

FIG. 4 illustrates the interrelation of therapy insights model development and downstream applications of the system of FIG. 1. S1-S6 represent the stages of the method of FIG. 3. The stages of the method of FIG. 3 may be involved in more than one of model development and downstream applications of the system.

Figure 5:
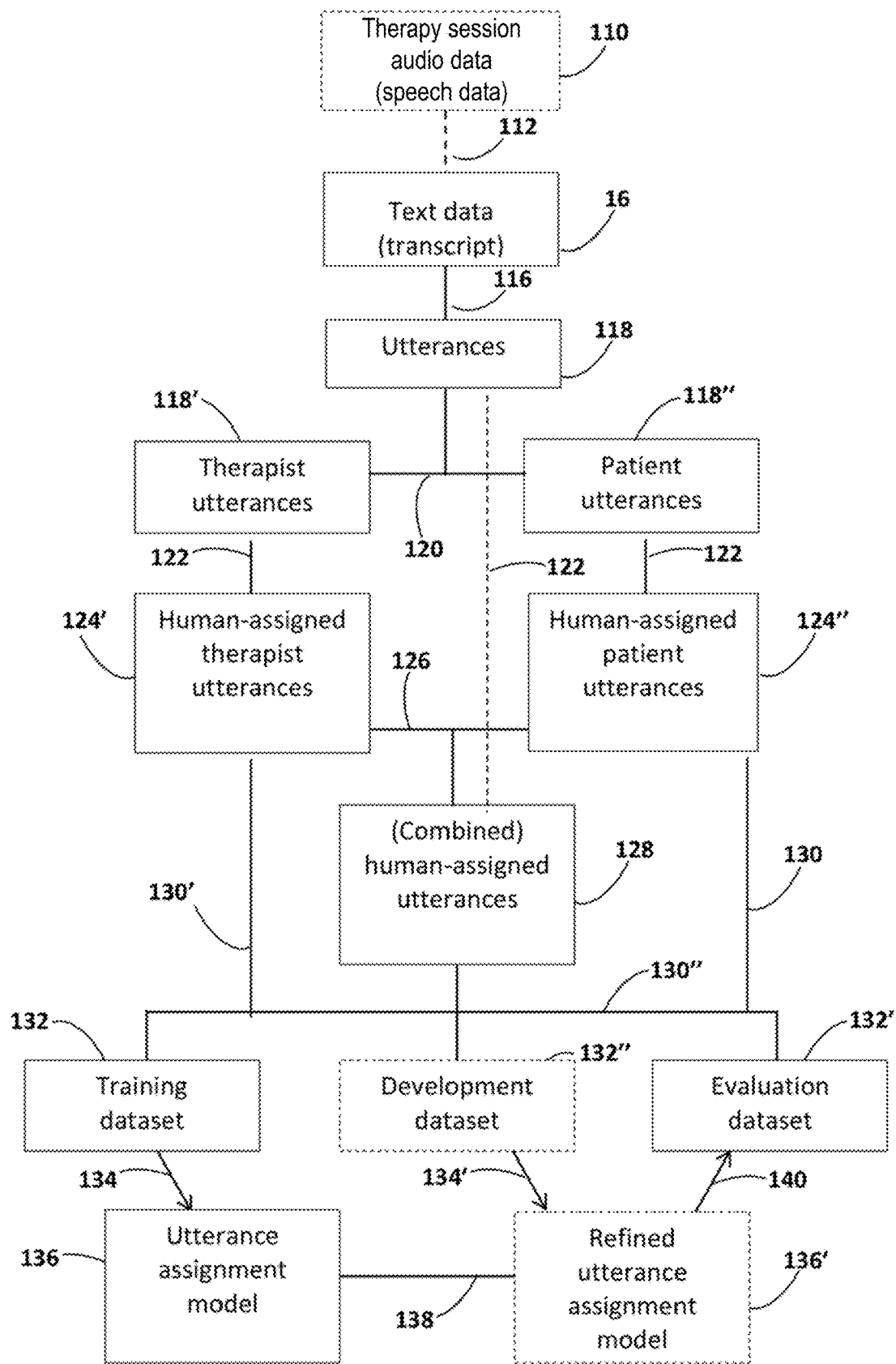

FIG. 5 illustrates an exemplary development method of an utterance assignment model (the first part of a therapy insight model) which may form part of the system of FIG. 1 or a method of the invention.

Figure 6:
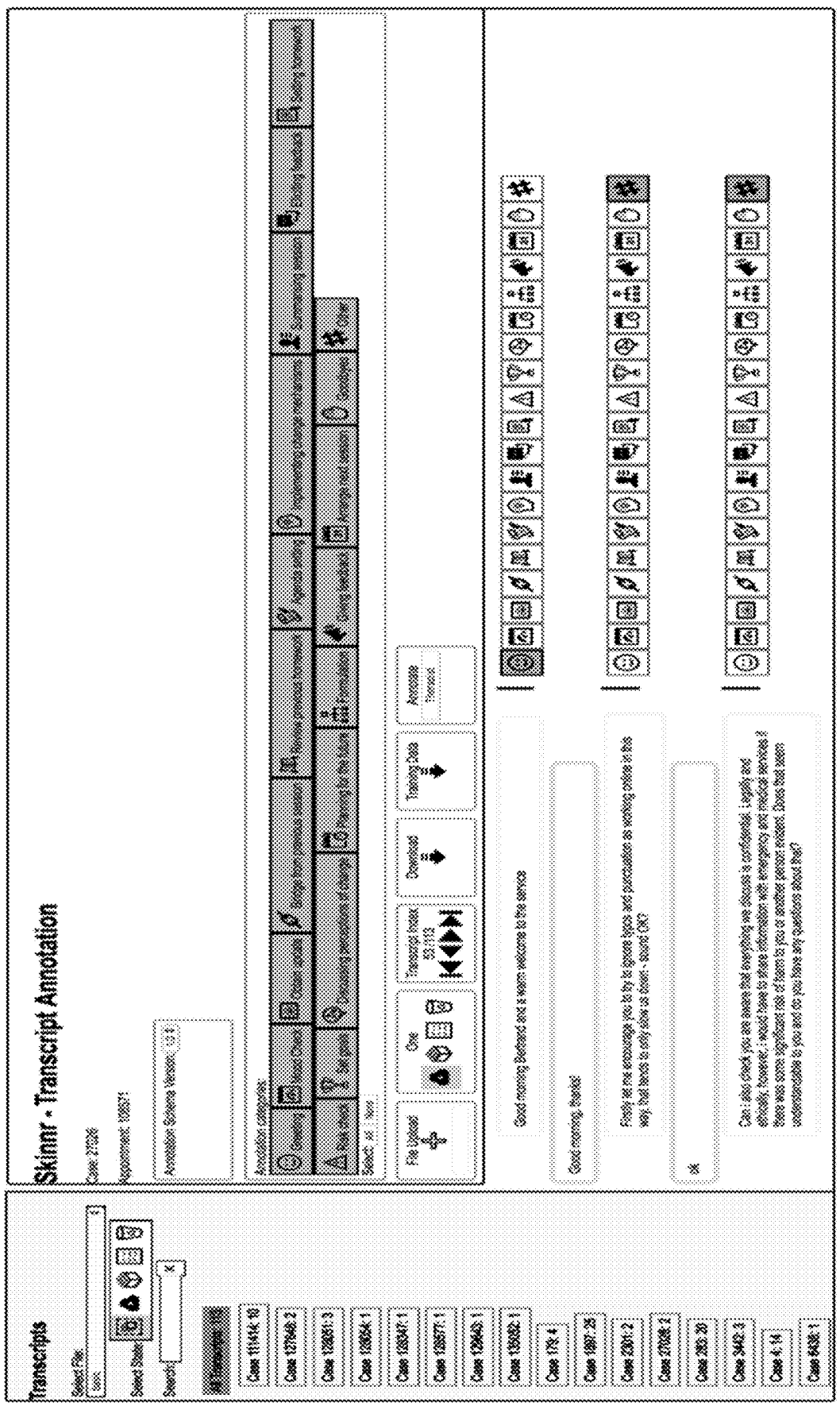

FIG. 6 illustrates an interface of the Skinnr tool. This tool may be used for the gathering of manually-annotated (tagged) utterances when a classification (tagging) model is used in the method of FIG. 5 or the system of FIG. 1.

Figure 7:
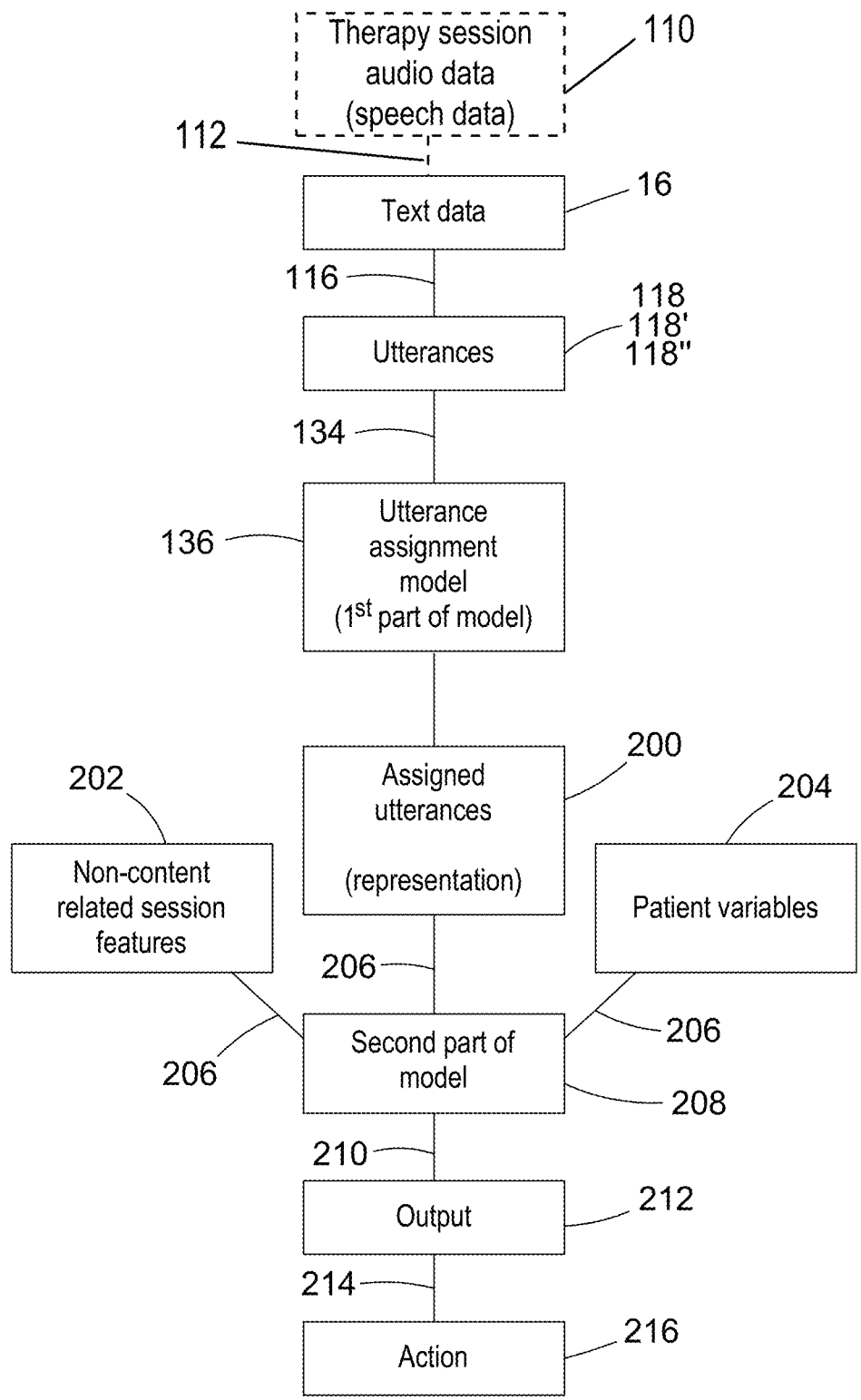

FIG. 7 illustrates an exemplary prediction phase of the method of FIG. 3.

Figure 8:
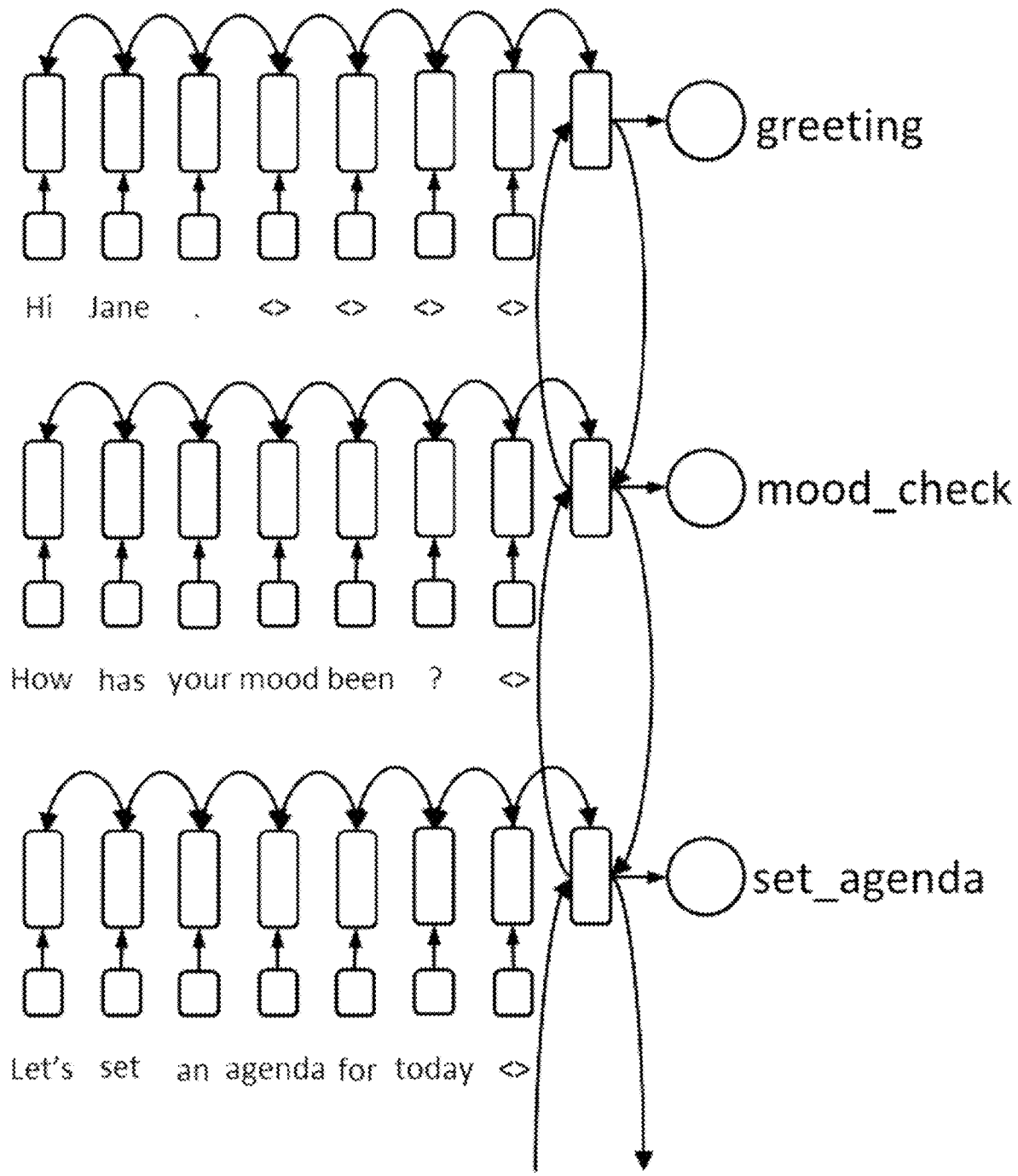

FIG. 8 is a high-level illustration of an utterance assignment (classification) model (first part of a therapy insights model (TIM)) architecture when tagging is used to assign meaning to utterances.

Figure 9:
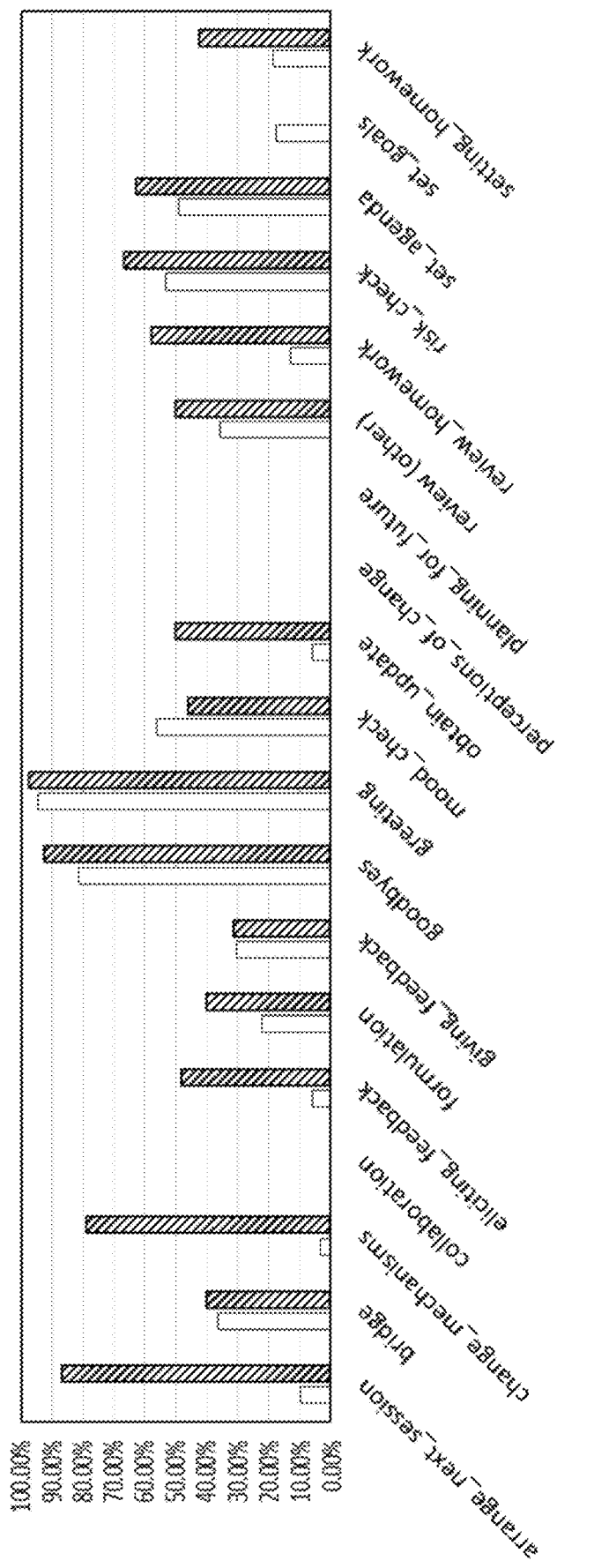

FIG. 9 shows early utterance assignment (classification) model performance in comparison with regex classification. The utterance assignment (classification) model was trained using 80 transcripts and evaluated on 20 others, F1 is used as a measure of utterance assignment (classification) model performance in comparison with manual annotation of utterances with tags. The machine learned model (HiBiLSTM; Hierarchical Bidirectional LSTM) outperformed regexes (Reg).

Figure 10:
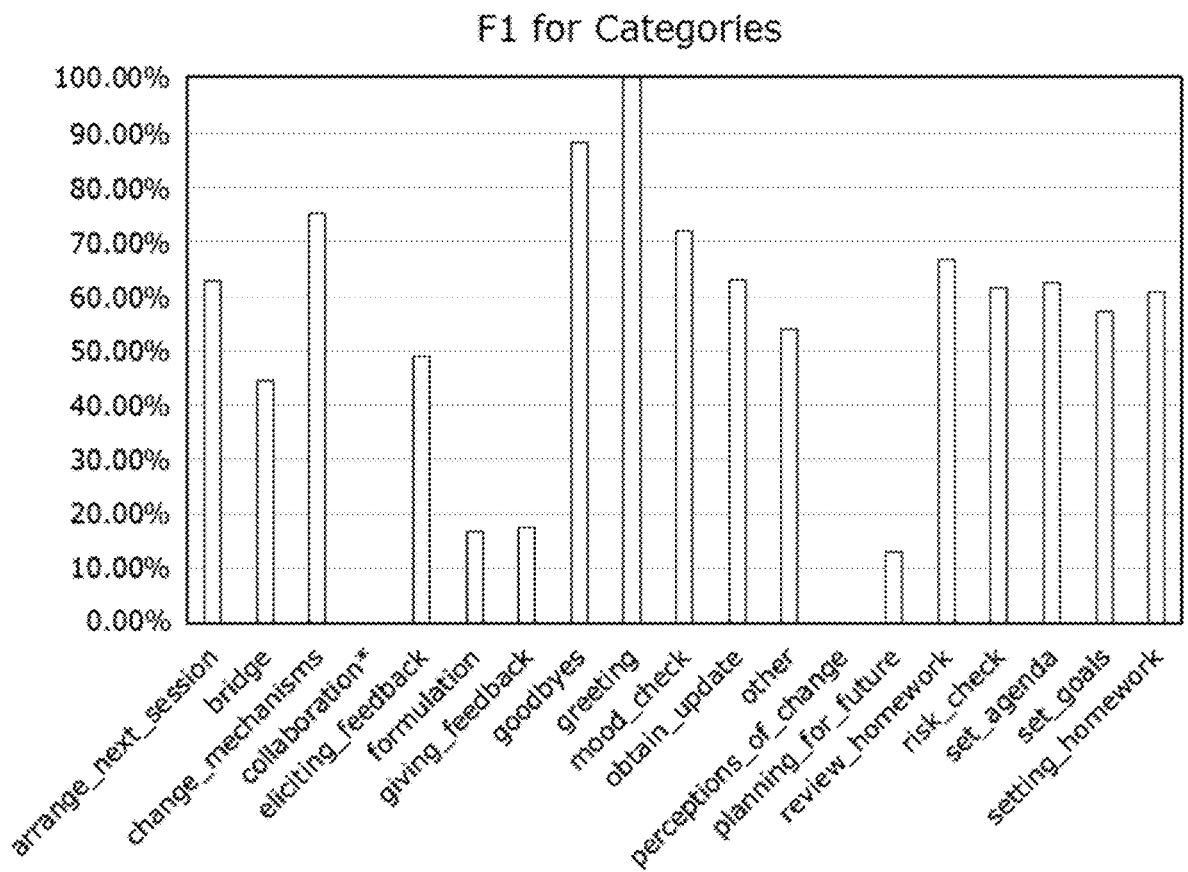

FIG. 10 shows early performance measures of an utterance assignment (classification) model (HiBiLSTM; first part of the therapy insights model). F1 is used as a measure of utterance assignment model performance in comparison with human annotation.

Figure 11A:
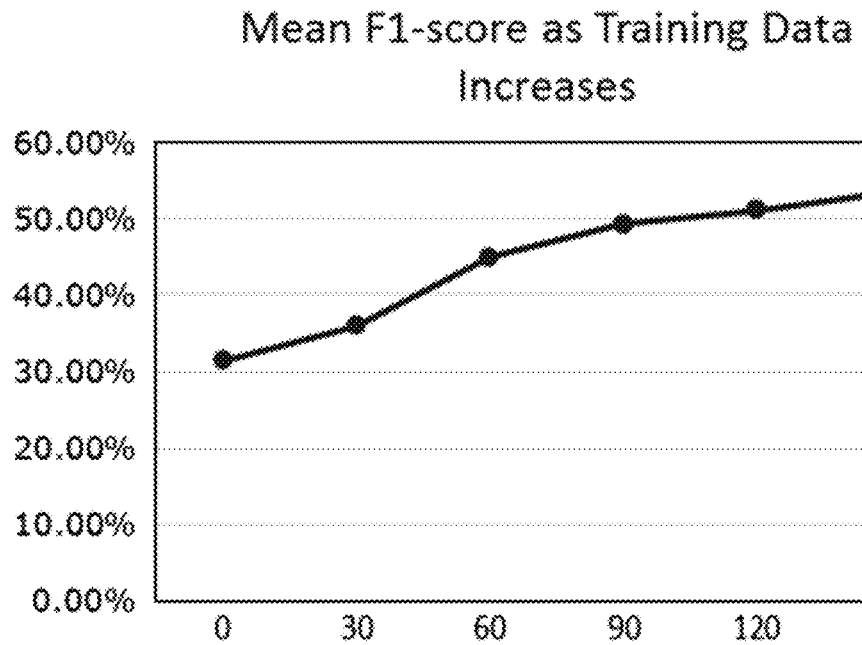

FIG. 11a shows the overall F1 measure for an utterance assignment (classification) model (HiBiLSTM; first part of the therapy insights model (TIM)) as a function of training dataset size. The X-axis shows hours of therapy used to train the model.

Figure 11B:
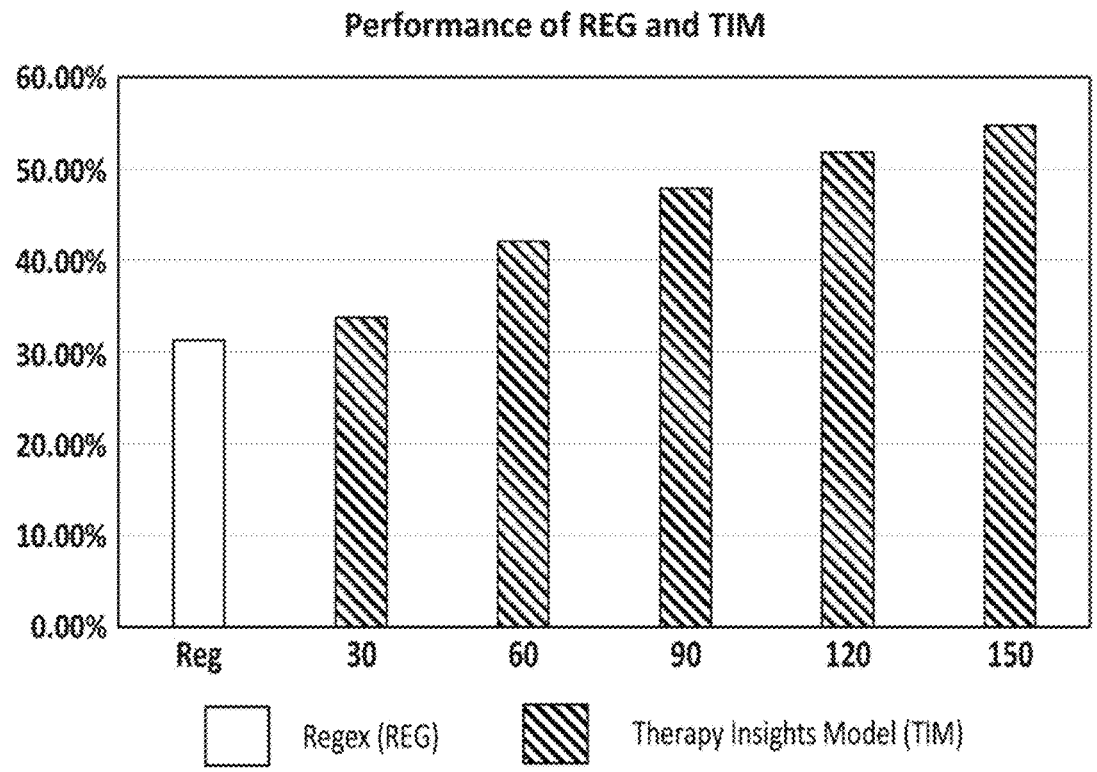

FIG. 11b shows overall F1 measure for an utterance assignment (classification) model (HiBiLSTM; first part of the therapy insights model (TIM)) as a function of training dataset size and compared with Regex annotation. The X-axis shows the performance of the Regex-based system (REG), or hours of therapy used to train the utterance classification model in this example.

Figure 12:
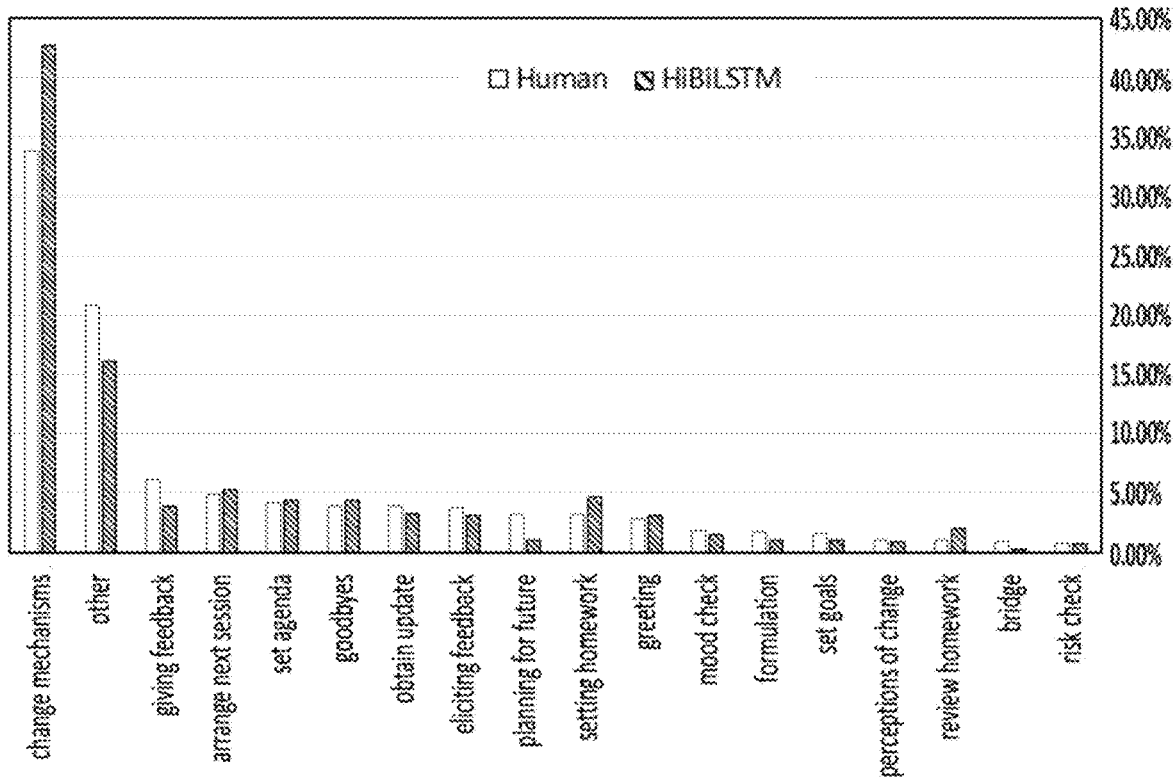

FIG. 12 shows a distribution of therapist utterance types as identified by an utterance assignment (classification) model (first part of the HiBiLSTM therapy insights model) or by human annotation.

FIG. 13 shows a correlation between number of therapist utterances of a particular assigned category as classified by the first part of the HiBiLSTM therapy insights model and clinical outcome in patients. In each chart, the number of utterances is expressed as the mean number of utterances of that category per therapy session (x-axis), whilst the clinical outcome is expressed as the percentage of patients who show clinical improvement ('% improvement') for therapy sessions of a given utterance amount. The dashed horizontal line represents the average clinical improvement rate of 65% (the percentage of all cases that improve during treatment). FIG. 13a: clinical improvement correlated with amount of 'agenda setting' utterances per session. FIG. 13b: clinical improvement correlated with amount of 'change mechanism' utterances per session. FIG. 13c: clinical improvement correlated with amount of 'eliciting feedback' utterances per session. FIG. 13d: clinical improvement correlated with amount of 'risk check' utterances per session.

Figure 14:
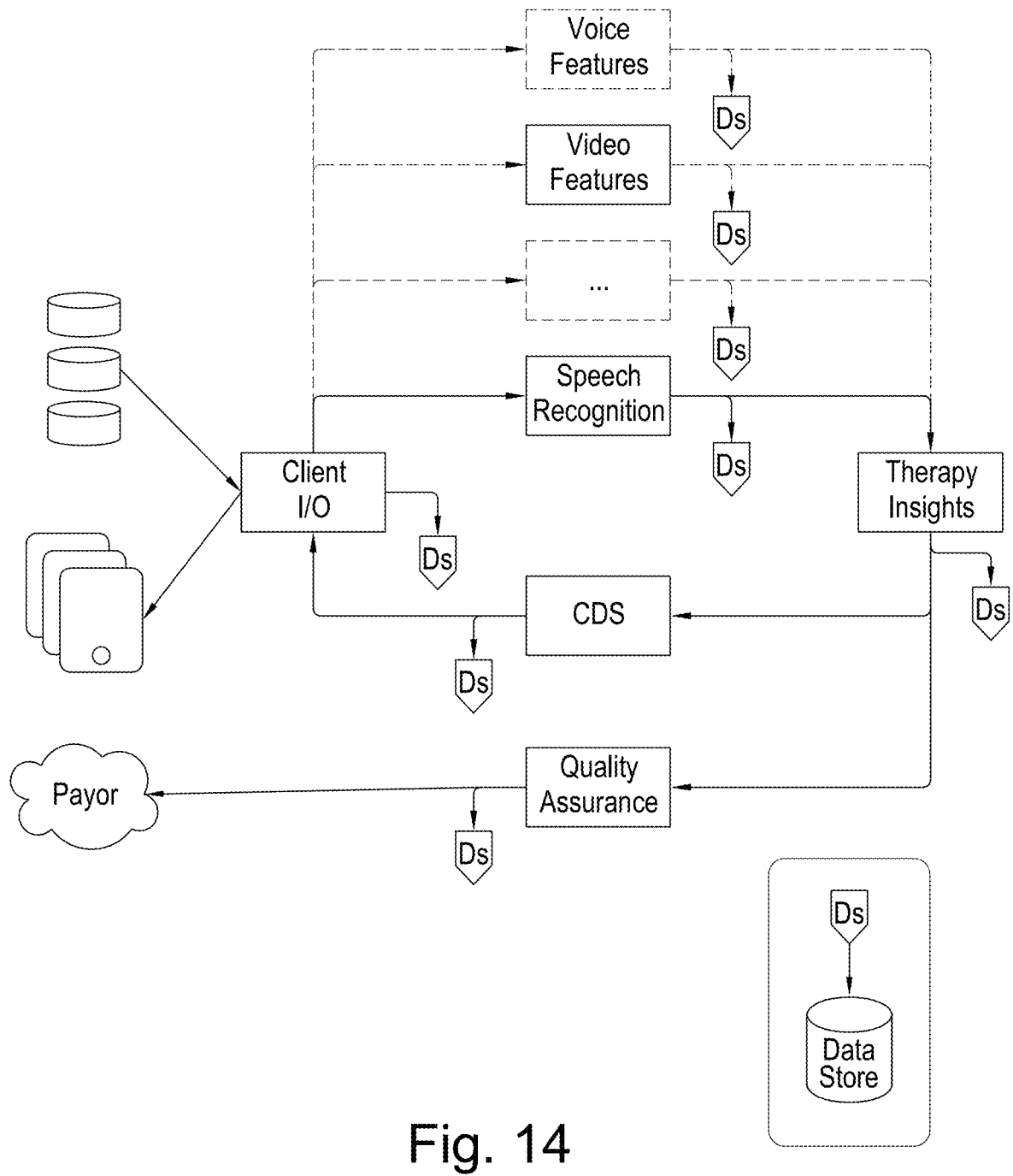

FIG. 14 illustrates a system for taking one or more actions relating to therapy. 'Client I/O' indicates client (patient) input/output, 'Ds' indicates output to a data store, CDS indicates Clinical Decision Support.

Outcomes for many mental disorders have stagnated since the original treatments were developed and in some cases the efficacy of psychotherapy appears to be reducing over time. One of the reasons for the gap in quality of care is the lack of systematic methods for measuring quality in the delivery of psychotherapy. As with any evidence based intervention, in order for treatment to be effective it needs to be delivered as intended (also known as treatment integrity). Improving the effectiveness of psychotherapy is therefore dependent upon accurate measurement of how treatment is delivered. However, while it is relatively simple to monitor the integrity and delivery of most medical treatments (e.g. the dosage of a prescribed drug), monitoring the delivery or 'dosage' of psychotherapy is a significantly greater challenge. Most psychotherapeutic treatments comprise a series of private discussions between the patient and clinician. Monitoring the delivery of this type of treatment to the same extent as physical medicine has previously required infrastructure and resources beyond the scope of most healthcare providers.

NICE (National Institute for Heath and Care Excellence) and the APA (American Psychological Association) currently recommend Cognitive Behavioural Therapy (CBT) as a treatment for most common mental health problems, such as depression and anxiety-related disorders. CBT refers to a class of psychotherapeutic interventions informed by the principle that mental disorders are maintained by cognitive and behavioural phenomena, and that modifying these maintaining factors helps produce enduring improvements in patient's presenting symptomology. One third of patients referred to the Improving Access to Psychological Therapies (IAPT) programme in the National Health Service in England in 2016/2017 received CBT, and CBT is among the most common treatment types offered to patients in the US. Despite its widespread use, IAPT currently includes no objective measure of treatment integrity for CBT, while only 3.5% of psychotherapy randomized controlled trials (RCTs) are reported to use adequate treatment integrity procedures.

CBT is the most researched form of psychotherapy and is described as an "evidence based" treatment, however the vast majority of "evidence" refers to measures of treatment outcomes; with relatively few studies investigating the mechanisms of treatment. Quantifiable measures of treatment delivered are needed not only to develop an understanding of the relationship between the 'dosage' of specific aspects of CBT and outcomes, but also, for example, for the development of new psychological treatments needed for the large number of people who do not respond to existing interventions.

The CTSR (Cognitive Therapy Scale Revised (https://www.getselfhelp.co.uk/docs/CTSR.pdD) tool is the current standard instrument for measuring the competency of CBT practitioners, and is used in both the UK and USA, for example. It is a manual tool whereby a supervisor assesses the competency of a therapist by marking 12 quality items on a 0-6 scale according to how well the therapist displayed those quality items during a particular treatment session. Prior to the development of the CTSR, a previous version, the CTS, was used. Due to the way the CTSR assessment is carried out, and the consequent supervisor time necessitated by this, the assessment is usually only applied to a limited number of therapy sessions. Therefore therapist competency is not assessed for the vast majority of therapy sessions delivered. Furthermore, the quality of the measurement of therapist competency is itself dependent on the ability of the supervisor to use the CTSR scale (or other manual quality assessment measure) effectively. Therefore different supervisors may make divergent assessments of a particular therapy session/therapist competency using the existing manual assessment methods (i.e. inter-rater reliability may be low).

The traditional method of measuring the relationship between treatment delivered and outcomes is to use observational coding methods, typically involving the manual transcription of therapeutic conversations (interactions, interventions) or post-session therapist self-assessment. These are resource intensive exercises which typically means that most studies focus on the effect of a small number of therapeutic factors in a relatively a small sample of patients. To investigate the effect of specific therapeutic factors (or components), previous studies have typically added or removed a component of therapy and measured the effect of this manipulation on outcomes. As with all RCTs, the results of these experimental interventions are difficult to transfer to 'real world' psychotherapy and require sample sizes that are larger than typically used. Improved methods of quantifying treatment delivered must therefore be able to simultaneously measure multiple factors of a therapy session, be applied in a natural clinical context, and be gathered from a sufficiently large enough sample to draw meaningful conclusions.

In order to apply the invention to a therapy session where the interaction between the therapist and the patient comprises a spoken, e.g. face-to-face, conversation or dialogue (intervention), it is necessary to supply means of obtaining data relating to the conversation, i.e. a device for recording or extracting speech from the therapy session.

Computer-Based System (Computer-Implemented System, Device or Apparatus)

Referring to FIG. 1, a computer-based system 1 for providing therapy includes a plurality of devices $2_1 \ldots 2_N$ connectable to a server 3 via a network system 4.

Online therapy, including internet-enabled cognitive behavioral therapy (IECBT), currently offers significant advantages over standard care. Internet-enabled cognitive behavioral therapy is a type of high-intensity online therapy used within an Improving Access to Psychological Therapies (IAPT) program. Within IAPT using IECBT, patients are offered scheduled one-to-one sessions with an accredited therapist, similar to face-to-face programs, whilst also retaining the advantages of text-based online therapy provision including convenience, accessibility, shorter waiting times, increased disclosure and subsequent access to therapy session transcripts. In this context, a patient is an individual who has been referred or has self-referred to the therapy program or service. A computer-based system for providing IECBT therapy is described in WO 2016/071660 A1 (which is hereby incorporated by reference). The improvement rate for patients treated with IECBT is significantly higher than for severity-matched patients treated with standard (face-to-face) care. The provision of IECBT therapy also permits the collection of transcript data relating to text-based online therapy sessions, transcript data that may be processed and correlated with therapy outcome in order to obtain information about the content of effective therapy.

It would be beneficial to patients, therapists, therapy services and insurance companies to apply the additional benefits and improved outcomes of IECBT to face-to-face therapy sessions. This requires the acquisition of data relating to the therapy session, e.g. audio data (including speech data) from the spoken conversation between therapist and patient(s) in a face-to-face therapy session.

Therefore the system 1 preferably enables the acquisition of audio data (including speech data) during a face-to-face therapy session using one or more device 2, the analysis of such data and the automated provision of actions as appropriate.

Each device 2 may be an audio input device such as one including a microphone or microphone array, optionally a digital microphone or digital microphone array. Each device 2 may be a mobile device, such as a smartphone, tablet, smart speaker, speakerphone, wearable device, laptop, etc. Each device 2 may be a (nominally) non-mobile device, such as a fixed e.g. wall or ceiling microphone, desktop computer, etc. Each device 2 may be of any suitable type, such as a ubiquitous audio input/sound recording or computing device, etc. The device 2 may or may not have a speaker (audio output).

Figure 2A:
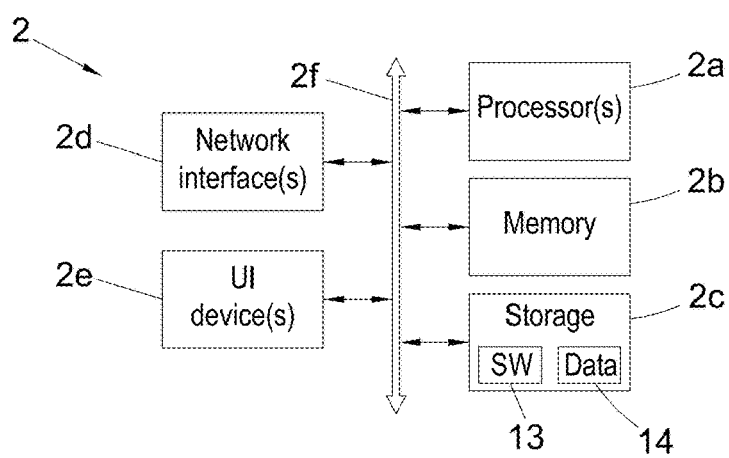
FIG. 2a illustrates a device which may form part of the system of FIG. 1.

Referring to FIG. 2a, a (typical) device 2 includes one or more processors 2a, memory 2b, storage 2c, one or more network interfaces 2d, and one or more input (e.g. user interface) devices 2e. The one or more processors 2a communicate with other elements of the device 2 via one or more buses 2f, either directly or via one or more interfaces (not shown). The memory 2b includes volatile memory such as dynamic random-access memory. Among other things, the volatile memory is used by the one or more processors 2a for temporary data storage, e.g. when controlling the operation of other elements of the device 2 or when moving data between elements of the device 2. The memory 2b includes non-volatile memory such as flash memory. Among other things, the non-volatile memory may store a basic input/output system (BIOS). The storage 2c may include e.g. solid-state storage and/or one or more hard disk drives. The storage 2c stores computer-readable instructions (SW) 13. The computer-readable instructions 13 may include system software and application software. The application software may include a web browser software application (hereinafter referred to simply as a web browser) among other things. The storage 2c also stores data 14 for use by the device 2. The one or more network interfaces 2d communicate with one or more types of network, for example an Ethernet network, a wireless local area network, a mobile/cellular data network, etc. The one or more input devices 2e preferably include audio input devices such as one or more microphones, sensors, etc. Where the system 1 includes a microphone array, this may be present on a single device 2, or individual microphones may be present on a plurality of devices 2 to form an array. The one or more input devices 2e may include other input devices such as a keyboard, pointing device (e.g. mouse), a video input device e.g. a camera, and/or a touchscreen. Hence the device 2 is able to provide an input device, preferably an audio input device, for use during a face-to-face therapy session between e.g. a patient and a therapist that connects via a network system to a server. It is envisaged that such devices 2 may be present at a plurality of therapy sessions, including a plurality of therapy sessions delivered by one therapist, and/or individual therapy sessions delivered by a plurality of therapists.

Figure 2B:
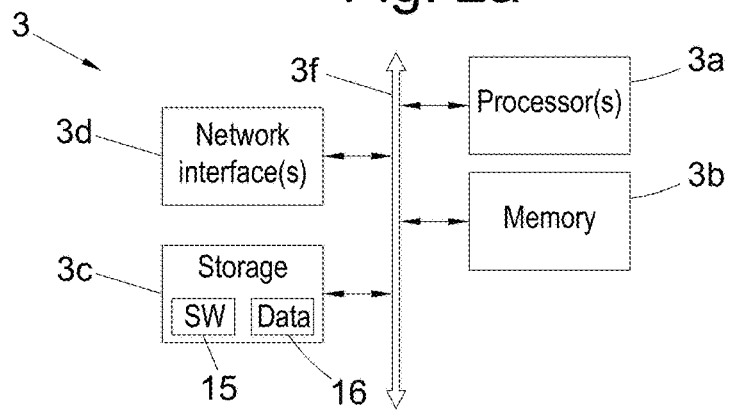
FIG. 2b illustrates a server which may form part of the system of FIG. 1.

The device 2 of the system 1 may include one or more output devices 2g for example a display and/or other output devices such as a loudspeaker. Hence the device 2 may provide an output device 2g, either for use during a face-to-face therapy session between e.g. a patient and a therapist, or at any point thereafter. The input device 2e and the output device 2g may be present on the same device 2, or may be present on different devices 2. In that way the different devices have flexible capabilities. For example one device 2 of the system 1 may include an (audio) input device that obtains audio data from a therapy session, whereas another device 2 of the system 1 may include a display that provides one or more of e.g. an automatically-generated therapist support process to the therapist, an automatically-generated therapist reallocation process to a supervisor of the therapist, or an automatically-generated transcript of the therapy session to the patient, the therapist, the therapy supervisor, the therapy service or the therapy payer (e.g. insurer). Referring to FIG. 2b, a (typical) server 3 may include one or more processors 3a, memory 3b, storage 3c, one or more network interfaces 3d, and one or more buses 3f. The elements of the server 3 are similar to the corresponding elements of the device 2. The storage 3c stores computer-readable instructions (SW) 15 (including system software and application software) and data 16 associated with the server 3. The application software may include a web server among other things. Alternatively/additionally, the server 3 may correspond to a virtual machine, a part of a cloud computing system, a computer cluster, etc.

Referring again to FIG. 1, the network system 4 may include a plurality of networks, including one or more local area networks (e.g. Ethernet networks, Wi-Fi networks), one or more mobile/cellular data networks (e.g. $2^{nd}$, $3^{rd}$, $4^{th}$ generation networks) and the Internet. Each device 2 is connectable to the server 3 via at least a part of the network system 4. Hence each device 2 is able to send and/or receive data (e.g. audio data constituting speech) to and/or from the server 3.

The computer-based or computer-implemented system (device or apparatus) may comprise one or more computer readable memory comprising one or more computer executable instructions, at least one computer processor operatively connected to the one or more computer readable memory, the at least one computer processor being configured to execute the one or more computer executable instructions to effectuate operations that comprise one or more methods of the invention as set out below.

Further, the invention may comprise a computer process for controlling a device (e.g. a system, an apparatus, a computer device, a mobile device, and/or a smartphone device) that includes at least an input device, at least one wireless communication unit, one or more computer readable memory including one or more computer-executable instructions, and at least one processor component operatively coupled to the one or more computer readable memory, the computer process including operations comprising one or more methods of the invention as set out below.

Method

Referring to FIG. 3, the system 1 may perform a method 10 comprising several steps S1-S6.

Training (Model Development) and Prediction Phases

Some steps of the method, particularly the third and fourth steps S3, S4, may be performed either as part of a training phase (FIG. 5) or as part of a prediction phase (FIG. 7).

The third and fourth steps S3, S4, each involve parts of a deep learning model. Such a model typically has model inputs, model parameters and model outputs.

Training data (hereinafter referred to as a training dataset) is used during the training phase. In some examples, the training dataset includes multiple instances of e.g. human-assigned data. During the training phase, the instances of data are provided as model inputs, and the model parameters are adjusted (i.e. the model is constructed) such that the (first part of the) model outputs optimally predict (assign) the corresponding semantic representations (e.g. labels, tags). All of the data in the training dataset is used collectively to construct the model.

During the prediction phase, an instance of unassigned (e.g. unlabelled, untagged, unclassified) data is inputted to the first part of the constructed model which outputs a corresponding prediction of the semantic representations (e.g. labels, tags, categories, classifications). A plurality of these assigned semantic representations are then formed (compiled) into a representation of the therapy session, which is then inputted to the second part of the model.

First Step of the Method

Referring in particular to FIG. 3, at a first optional step S1, the method 10 starts. The first step S1 may e.g. involve a user (a patient or a therapist) of a device 2 causing the device 2 to establish a communications session with the server 3.

The device 2 and/or the server 3 may enable the patient or therapist to register, to identify and authenticate themselves, etc.

Typically, one or more devices 2 and the server 3 communicate with one another during a communications session and run particular application software (for example one or more of: audio recording software, audio digitization software, audio conversion software, speaker diarization software, speech-to-text processing software, a web browser, a web server, further application software at the server 3, etc.).

In this way, a device 2 and the server 3 provide an audio input device, enabling the therapy session audio data (e.g. spoken conversation between therapist and patient) to be inputted to the system 1.

In a similar way, a device 2 and the server 3 may provide a user interface (e.g. a therapist interface, a patient interface, a supervisor interface, a payer interface) enabling a therapist, a patient, a supervisor or a payer to interact with the system 1. In this way, a device 2 and the server 3 may provide outputs and automated actions to the users.

Second Step of the Method

Referring in particular to FIGS. 3, 5 and 7, at a second step S2, the system 1 first obtains certain audio data 110. The audio data 110 relates to one or more therapy sessions. The one or more therapy session may be of any length. The audio data 110 is obtained from the one or more patient and/or from the therapist. Any audio data may be provided by the patient or the therapist. The audio data may comprise speech data (the content of spoken conversation). The speech data may be in English or in any other language. The therapy session may be any type of therapy session, for example a psychotherapy session, a talking therapy session, or a coaching session. The therapy session may be a one-to-one therapy session (one therapist and one patient), or may be a group therapy session (one therapist and more than one patient).

The original spoken conversation from a therapy session is analogue audio data that is converted to digital audio data by the system. Where the audio data 110 is obtained using one or more digital microphones a digital audio signal is directly outputted. Where the audio data 110 is obtained using one or more analogue microphones the analogue audio signal is converted to a digital audio signal by an analogue-to-digital converter (ADC) to produce the audio data 110.

The audio data 110 may comprise an audio stream derived from a single audio input e.g. microphone, or more preferably it may comprise a plurality of audio streams derived from a plurality of audio inputs e.g. a microphone array. Where the audio data 110 comprises a plurality of audio streams, this can be used to extract e.g. directionality information from the data.

As well as verbal, content-related data, the audio or speech data 110 may also contain non-verbal (non-content related) data 202, for example tone, pitch, volume, voice quality, rate, speaking style, as well as prosodic features e.g. rhythm, intonation, and stress. The method 10 may also use the non-verbal content of the audio data inputted.

Speaker diarization is the attribution of streams of input audio data (speech data) to the particular individuals taking part in a conversation. Speaker diarization may be mono-channel diarization (where a single audio channel is inputted from a single microphone), or multi-channel diarization (where multiple audio channels are inputted from a plurality of microphones e.g. a microphone array). Speaker diarization uses a combination of speaker segmentation, where speaker change points in the audio data are identified, and speaker clustering, where streams of speech (audio streams) are grouped together on the basis of characteristics of the speech. Speaker diarization uses algorithms to model the speech data using either 'Bottom-Up' or a 'Top-Down' clustering. In 'Bottom-Up' clustering the algorithm splits the audio data into a succession of clusters and progressively tries to merge the redundant clusters in order to find the point where each cluster corresponds to an individual speaker. 'Top-Down' clustering starts with a single cluster for all the audio data and splits it iteratively until the number of clusters equals the number of speakers.

Diarization may make use of a number of types of information in order to perform this attribution, including directional information (e.g. by using multichannel acoustic beamforming techniques to determine which direction the audio derives from relative to the audio input e.g. microphone array), and/or content information (by making use of differences in tone/pitch etc. between individuals taking part in the conversation). See Anguera et al., 2012, ("Speaker Diarization: A Review of Recent Research." *IEEE Transactions on Audio, Speech, and Language Processing* 20 (2012): 356-370.) for a review of speaker diarization techniques, which is hereby incorporated by reference. Other methods of attributing particular streams of audio data (audio streams) to the particular individuals taking part in a conversation (e.g. spoken therapy session) will be known to those skilled in the art.

The therapy session audio data (speech data) 110 is converted 112 to text data 16 (a transcript) by the system 1. The audio data may first be stored by the system 1 (as an audio recording), and then converted 112 to text data 16, which may also be stored by the system 1. Alternatively the audio data 110 may be converted 112 directly to text data 16 which is then subsequently stored by the system 1.

The acquisition of the therapy session audio (speech) data 110 occurs via one or more devices 2 with audio input 2e. The storage and subsequent processing and analysis of the data may be achieved by a combination of any parts of the system, including the device(s) 2 and the server 3 (e.g. a cloud-based server) communicating via the network system 4. Preferably, the device 2 with audio input 2e performs the acquisition of the audio data 110, and the server 3 (e.g. a cloud-based server) performs the analysis of the data.

Where pre-processing of the audio data 110 occurs on the device 2, for example processing to achieve noise reduction, or carrying out one or more elements of speaker diarization on the device, the pre-processed data plus metadata is then sent via the network system 4 to the server 3. Where no pre-processing of the audio data 110 occurs on the device 2, the one or more audio streams captured by the one or more audio input devices of the device(s) 2 are sent directly to the server 3 for subsequent processing and analysis.

The text data 16 may be obtained in any suitable way. Speech-to-text processing may be used to extract text from the audio signal. For example, any standard ASR (Automatic Speech Recognition) system may be used to convert 112 the sounds of speech (therapy session speech data 110) into words (text data 16). Diarization may be also used to augment the speech-to-text transcription (i.e. speaker attributed speech-to-text).

The text data 16 is divided 116 into utterances 118. The utterances represent short passages/phrases/sentences of speech. Where diarization is used to attribute a particular stream of input audio data to a particular speaker (e.g. therapist or one or more of the patient(s)), this may therefore be used to attribute each utterance in the exchange to either the therapist or to the one or more patient. If ASR is used to convert speech into words (text data) the ASR system may nominate portions of speech (e.g. divided by pauses) as individual utterances. Alternatively if the audio from a therapy session is transcribed into a contiguous transcript, this transcript may be subsequently divided into individual utterances using suitable software.

The utterances 118 from a therapy session may be divided 120 into therapist utterances 118' and patient utterances 118". Each utterance may be automatically identified as deriving from either the patient or the therapist by the use of e.g. diarization. Where diarization is used to separate the audio data into two or more audio streams before production of the transcript, the transcript preferably contains both the text (content) data and associated data relating to the speaker of particular sections of the text. Preferably, both sets of information are transferred when the transcript is divided into individual utterances, in order to produce e.g. patient utterances 118", and therapist utterances 118'.

Where a text transcript and/or individual utterances are produced without prior diarization of the audio data, the utterances may subsequently be associated with a particular speaker by any suitable method in order to produce e.g. patient utterances 118", and therapist utterances 118'.

Either the patient utterances 118", the therapist utterances 118' (or a combination of both patient utterances and therapist utterances) may be used in the methods of the invention.

Alternatively, where a contiguous transcript (text data) of a therapy session is formed without ascribing sections of text to either the therapist or the one or more patients, the invention may be performed on/with the totality of the text data.

Information relating to the relationship between individual utterances (the order of the utterances during the therapy session) may be retained along with the utterance and used in the methods and systems of the invention; this provides a richer source of information for use in classifying or assigning meaning to the utterances. Alternatively, the utterances used may be a pool of utterances, for example all utterances from within one therapy session, or from a plurality of therapy sessions delivered by a particular therapist, or from a plurality of therapy sessions relating to a particular patient, that have been stripped of their relationship information.

During a therapy session, the therapist and patient interact. The therapist poses questions or makes statements (together considered therapist utterances 118'), to which the patient then responds with patient utterances 118". Examples of therapist utterances are included in Table 2 below.

The method may also involve obtaining further data relating to the patient (this further data is referred to as patient data). The patient data may include data relating to patient variables 204, for example personal data such as age, gender, etc., medical data such as medication use, drugs/alcohol misuse, etc., and so forth. The patient data may be provided by the patient using a patient interface device 2 or may be obtained in any other suitable way.

Third Step of the Method

At a third step S3, semantic representations are assigned to the utterances to obtain assigned utterances 200.

This involves using deep learning processes which may be referred to as a (deep learning) utterance assignment model 136, or the first part or first portion of a (deep learning) therapy insights model.

Semantic representations (meanings) may be assigned to the utterances by the model 136 in a number of ways including:

Identification of speaker intent

Identification of speaker intent and identification of slots

Embedding in a semantic space

Classifying (tagging) utterances

Therefore assigned utterances are those to which a meaning has been assigned by any suitable method.

For example, a first part of a deep learning model may assign a semantic representation that encodes meaning to each of the plurality of utterances in context.

One such semantic representation is a distributed semantic representation which often consists of a fixed-size dense vector that can be used as input to other systems that can provide semantics on a more specific level (such as classification, sentiment analysis, and/or intent representation). The method may use these distributed semantic representations as input to a classification system which assigns one or more tags to an utterance. These tags convey the role that the utterance plays in therapy. However, more broadly these distributed semantic representations can also be used as input to a system to determine the sentiment of the utterance (e.g. positive, neutral, negative) or tone of an utterance (e.g. confident or tentative). Furthermore, the distributed semantic representations can be used as input to a system that translates the utterance into an intent representation. An intent representation encapsulates an action or goal that the speaker wishes to achieve and can be associated with optional or required parameters.

The development of an utterance assignment model may be understood by reference to FIGS. 5 to 8. Referring in particular to FIG. 5 which illustrates an exemplary development (learning, training) phase of a utterance assignment model, following the division 116 of the text data 16 into utterances 118, which optionally may further be divided 120 into therapist utterances 118' and/or patient utterances 118", the utterances are manually-assigned (with a semantic representation) 122 to produce human-assigned utterances. The human assigned utterances may comprise human-assigned therapist utterances 124', or human-assigned patient utterances 124", or combined human-assigned utterances 128. Combined human-assigned utterances 128 may be produced by manually-assigning 122 the (original, undivided) utterances 118, or by combining 126 the human-assigned therapist utterances 124' and the human-assigned patient utterances 124".

For example, human-assigned utterances may be produced by manually allocating each utterance to one of a plurality of suitably designed tags (categories). Examples of suitable tags and their design rationale may be found in Examples 1 and 5 below. The suitability of the tags will be determined by the particular characteristics of the input data, and may be determined empirically. One example of a system that may suitably be used for manual annotation is presented in FIG. 6.

Following manual assignment to semantic representations 122, the human-assigned utterances 124', 124", 128 are divided 130, 130', 130" into one of a training dataset 132, an evaluation dataset 132' or optionally a development dataset 132". The training dataset 132 may be used to train 134 a deep learning utterance assignment model (this may also be referred to as the first part of the therapy insights model (TIM)). Following training 134 of the utterance assignment model 136 using the training dataset 132, the utterance assignment model 136 may optionally be further refined 138 by performing fine-tuning of training hyper parameters 134' using the development dataset 132". The performance of the utterance assignment model 136 or the refined utterance assignment model 136' may be evaluated using the evaluation dataset 132', which the utterance assignment model had not previously encountered.

If after training and/or evaluation the particular utterance semantic representations (e.g. categories, tags) designed do not appear to provide appropriate granularity of information relating to the therapy session transcripts (e.g. too many utterances are allocated to one or more semantic representations), the semantic representations used may be refined by the inclusion of one or more level of sub-representation (for example slots relating to a particular intent). The model may thus be retrained using these one or more levels of sub-representations, in order to provide more detailed information relating to the transcripts/utterances.

Optionally, the utterance assignment model 136, 136' may use active learning to identify transcripts that it finds difficult to assign meanings to (i.e. where the model finds it difficult to assign a plurality of utterances to one or more semantic representations with a high degree of certainty). These transcripts may be automatically recommended by the model for manual assignment. Such manually-assigned transcripts may be used to refine 138 the semantic representation assignment performance of the model 136, 136'. Alternatively, the new manually-assigned transcripts may be added to the training dataset 132, and the training 134 of the utterance assignment model 136 may be re-run.

In one non-limiting example of the development of an utterance assignment model, following the division 116 of the text data 16 into utterances 118, which optionally may further be divided 120 into therapist utterances 118' and/or patient utterances 118", the utterances are assigned by human/manual annotation with tags ('tagged') 122 to produce human-annotated utterances. The human-annotated utterances may comprise human-annotated therapist utterances 124', or human-annotated patient utterances 124", or combined human-annotated utterances 128. Combined human-annotated utterances 128 may be produced by manually-annotating ('tagging') 122 the (original, undivided) utterances 118, or by combining 126 the human-annotated therapist utterances 124' and the human-annotated patient utterances 124".

In this example, the human-annotated (tagged) utterances are produced by manually allocating each utterance to one of a plurality of suitably designed tags (categories). Examples of suitable tags for both therapist and patient utterances and their design rationale may be found in Examples 1 and 5 below. The suitability of the tags will be determined by the particular characteristics of the input data, and may be determined empirically. One example of a system that may suitably be used for manual annotation is presented in FIG. 6.

Assigning a semantic representation to the utterances involves using the first part or portion of a deep learning model. The first part of the deep learning model may include a single layer or multiple stacked layers. The layers may be of various types, such as convolutional neural network layers (see Y. LeCun, L. Bottou, Y. Bengio and P. Haffner, "Gradient-based learning applied to document recognition," Proceedings of the IEEE, vol. 86, no. 11, p. 2278, 1998; hereby incorporated by reference), recursive or recurrent neural network layers, long short-term memory layers (see S. Hochreiter and J. Schmidhuber, "Long short-term memory," Neural computation, vol. 9, no. 8, p. 1735, 1997; hereby incorporated by reference), fully connected neural network layers, drop-out layers, and various nonlinearities such as sigmoid, tanh, ReLU, etc.

A deep neural network (DNN) refers to an artificial neural network endowed with complex structure. A convolutional neural network (CNN) is a type of DNN developed for object recognition in images. Recent research suggests that CNNs can also be applied to text (for example the text of a transcript derived from conversation audio data), where they can spot linguistic indicators. CNNs ignore most text structure and are only sensitive to very local dependencies. A recurrent neural network (RNN) is a type of DNN that is sensitive to text structure. RNNs are particularly effective at encoding the semantics of short- and medium-length text snippets (up to a sentence). RNNs do not currently work very well on whole documents, although recent developments (e.g. RNNs with attention) attempt to address this issue. Hierarchical applications of RNNs are another way of addressing this shortcoming. One possible type of hierarchical RNN application is where one RNN focuses on the words in an utterance, while another one uses whole utterance representations as inputs.

The deep learning model may be a bidirectional long short-term memory (BiLSTM) neural network; this type of network may be beneficial when the relationship between individual words within an utterance is important for assigning meaning (classification). More specifically, the model may be a hierarchical bidirectional long short-term memory (HiBiLSTM) neural network. When assigning a meaning to (classifying) a particular utterance, the HiBiLSTM model has access to the information from all utterances in the transcript in the correct positions. This allows information from the utterance itself and from surrounding utterances to be used by the machine learning model. By incorporating hierarchical relationship data it is possible to assign meaning to an utterance by taking into account the content of the utterance and also the context of other neighbouring utterances (e.g. a 'mood_check' utterance tends to occur after a 'greetings' utterance. The use of a model capable of synthesizing data combination of multiple types of data leads to better assignment (e.g. classification) and prediction by the model. FIG. 8 illustrates an exemplary HiBiLSTM model architecture.

Where suitable, another possibility is to use an utterance assignment model that does not use deep neural networks, employing instead simpler machine learning methods such as SVM (Support Vector Machines), logistic regression, decision trees, or other more complex techniques, such as random forests, or Bayesian graphical models.

Once the utterance assignment model 136, 136' has been trained 134, 134' with the manually (human)-assigned (e.g. tagged) data (the training dataset 132 and optionally the development dataset 132"), it may be used to assign semantic representations to the utterances present in additional (previously unseen) therapy session data.

Assignment of semantic representations to utterances by the trained model may be more consistent than that achieved manually by human assignors (annotators). This is because there may be noise among human annotators (i.e. two humans will not agree 100% of the time on the task; inter-annotator variability), and also because a human annotator may not assign the semantic representations consistently (intra-annotator variability). Assignment of semantic representations to utterances by the trained model is unbiased and repeatable. The model is also capable of assigning utterances at a much faster rate than that achievable by human annotators. For example, when assigning semantic representations to utterances by tagging, experienced human annotators may be able to classify around 11,000 utterances (equivalent to ~290 hours of therapy session text data) in 200-500 person-hours, whereas the utterance assignment model (an utterance classification model in this case) can classify approximately 4 million utterances (equivalent to 100,000 hours of therapy) in about 45 minutes.

The absolute number of utterances assigned as belonging to a particular semantic representation for a particular therapy session is an example of a content-related (therapy) session feature. Other examples of content-related session features may be the proportion of utterances from a therapy session transcript assigned to a particular semantic representation, or the frequency of utterances assigned with a particular semantic representation in a given unit time, where the unit time is less than the length of the whole therapy session. Other examples of session features may be found in Example 4 below. The combined one or more content-related session features relating to a therapy session may be referred to as a representation of the therapy session. The representation of the therapy session may be formed by compiling the plurality of assigned utterances.

The representation (e.g. one or more session features, tagged utterances) of a therapy session may be outputted 206 by the first part of the model in real-time (live) whilst a therapy session is ongoing, or ex post facto after the session has ended.

Fourth Step of the Method

Referring again to FIG. 3 and FIG. 7, at a fourth step S4, a second part of the model 208 (e.g. second part of the HiBiLSTM therapy insights model) is used to make 210 a prediction about the patient, the therapist and/or the therapy process. At least one classification/regression process is used to obtain (provide) an output 212 predicting a characteristic of the patient, the therapist and/or the therapy process (an output prediction). The output (prediction) may also be referred to as a hypothesis. The output may represent a correlation with at least one characteristic of the patient (e.g. likelihood of recovery), the therapist (e.g. quality of therapy delivered) and/or of a related therapy process (e.g. quality), as generated by at least one classification/regression process of the method.

A classification process is a machine learning process that associates categorical labels with input data. A regression process is a machine learning process that associates numerical labels/values with input data.

The one or more classification/regression processes may be referred to as the second part of the deep learning model 208 (second part of the HiBiLSTM therapy insights model). The one or more classification/regression processes may also be referred to as the classification/regression portion of the deep learning model. Analysis will be understood to mean the performance of classification and/or regression.

Using the deep learning model (HiBiLSTM therapy insights model), certain therapy session features (including content-related and/or non-content-related) and optionally patient variables may be correlated with a characteristic of the patient, the therapist and/or the therapy process, for example a clinical measure of the patient. Examples of characteristics may include clinical measures such as a patient's likelihood of recovery, likelihood of improvement, or engagement. The one or more content-related session features may be considered a representation of the therapy session. For example, the assigned utterances (utterances with associated meanings or semantic representations) outputted from the first part of the deep learning model (the utterance assignment portion of the model) may be used as the input to the second part of the deep learning model which outputs e.g. a prediction of clinical improvement based on the (totality of the) assigned utterances (representation) inputted. Other inputs to the second part of the deep learning model may include non-content related session features and/or patient variables.

Clinical improvement as used herein is defined as a patient achieving a statistically significant decrease in symptom severity, as measured on the PHQ-9 and GAD-7 scales. This is the definition used by NHS England in IAPT. Recovery as used herein is defined as the severity of symptoms of a particular patient decreasing to be below the clinical threshold on a clinically suitable scale, such as PHQ-9 or GAD-7.

The deep learning model may be used in combination with a logistic regression model of therapy outcome to correlate certain therapy session features, and optionally patient variables, with patient recovery.

The deep learning model may be used in combination with a logistic regression model of therapy outcome to correlate certain therapy session features, and optionally patient variables, with patient engagement.

The deep learning model may be used in combination with a linear regression model of therapy outcome to correlate certain therapy session features, and optionally patient variables, with patient symptoms or recovery.

A group of therapy session transcripts may be pooled for analysis, for example those deriving from a particular patient, a particular patient group, a particular therapist or a particular therapist group may be pooled. Analysing data for a particular group may provide group-specific correlations.

All transcripts for a single case (patient) may be pooled, and the value obtained of one or more session feature (averaged across all pooled transcripts for that case). The values for the one or more session feature (i.e. the representation of the therapy session) may be entered into a logistic regression with treatment outcome (e.g. whether the patient (case) recovered) as a binary outcome.

One example of a (content-related) session feature is the number of utterances that have been assigned to a particular semantic representation. For example, in the case of tagged utterances, those tagged with a particular category, e.g. the category/tag 'eliciting feedback'.

By using a large dataset, the second part of the deep learning model (the second part of the HiBiLSTM therapy insights model) may establish statistically significant correlation(s) between the representation of the therapy session (comprising one or more session features e.g. the number of utterances assigned to a particular meaning) and a characteristic of the patient, the therapist and/or of a related therapy process, e.g. treatment outcome. By selecting a dataset that relates to a particular group of therapy sessions (e.g. relating to a particular patient cohort), correlations specific to that group may be established.

Once these correlation(s) have been established bythe second part of the deep learning model (second part of the HiBiLSTM therapy insights model) the second part of the model may be used to make predictions based on the representation (one or more session features) of other (previously unseen) therapy sessions.

The prediction of a characteristic for a therapy session (output prediction) may be outputted (provided) by the second part or portion of the deep learning model (second part of the HiBiLSTM therapy insights model) in real-time (live) whilst a therapy session is ongoing, or alternatively ex post facto after the session has ended.

Thus the first and second parts of the model may be used together to analyse the therapy session, model predicted therapy session features (e.g. numbers of utterances assigned with a particular meaning, e.g. tagged as belonging to one or more category) and predict therapy session outcome (e.g. likelihood of patient recovery). The model as a whole may be used in real-time (live) whilst a therapy session is ongoing, or ex post facto after the session has ended Fifth Step of the Method Referring in particular to FIG. 3 and FIG. 7, at a fifth step S5 one or more actions are taken based on the one or more outputs of the fourth step S4.

As a simple example, an automated action may involve automatically providing a prediction of a characteristic of the patient, the therapist and/or the therapy process. The prediction may be provided to one or more of e.g. a therapist, a therapy supervisor (e.g. an experienced therapist), a therapist's employer, a healthcare service or a health insurance company. The prediction may be automatically provided via a therapist interface, or one or more other suitable interface(s).

The interface(s) may provide a display including one or more session features (a representation of a therapy session) and/or a prediction of therapy outcome based on the session features/representation. The display may also include confidence scores for the predictions. The display may include text and/or graphical representations of the predictions and confidence scores.

Automated Therapist Support

The deep learning model (HiBiLSTM, therapy insights model) may provide automated feedback to a therapist on the quality of the therapy session (e.g. likelihood of improvement of the patient), such that one or more actions may be taken by the therapist e.g. alterations to the current therapy session and/or future therapy sessions. The feedback may be provided to the therapist after completion of the therapy session in order that future therapy sessions may be improved, or alternatively/additionally whilst the therapy session is ongoing (real time or live feedback) so that the therapist may elect to change their current behaviour in order to increase the likelihood of the current therapy session having an improved outcome. In this way the quality of the therapy delivered may be improved and the current patient/future patients are more likely to show good clinical outcome (likelihood of recovery is increased). The method or system may automatically direct the therapist to take actions that are known or expected to result in improvement of the therapy provided.

All session features analysed (the therapy representation) may be provided to the therapist, or alternatively only those session features that indicate below-average performance of the therapist (i.e. where a prediction of low likelihood of good patient outcome is made by the model) may be presented to the therapist. By way of non-limiting example, the utterances forming the transcript of a particular therapy session are assigned to a particular semantic representation using an utterance assignment model, and the number of utterances of each meaning is determined to form session features. One or more session features known to correlate with patient outcome is selected. For example, when assigning meaning by tagging utterances, those utterance categories described in Example 4 below as showing either a positive or a negative correlation with likelihood of patient recovery is selected. Each session feature is compared with a suitable predetermined threshold or criterion.

The threshold or criterion is determined in any suitable way so as to provide a meaningful separation of different likelihoods of patient outcome. The threshold/criterion may be adjusted to balance the risks of false positives and false negatives. For different levels of control, more or fewer thresholds/criteria may be defined as desired. Data from a cohort of patients of known outcome (e.g. recovery) may be used to set the threshold(s)/criteria; the threshold(s)/criteria may then be applied to a matched cohort of new patients.

For example, where the selected session feature relates to an utterance semantic representation category known or suspected to correlate positively with likelihood of patient recovery, the predetermined threshold or criterion is set at a desired minimum level (a predetermined minimum threshold), for example the minimum amount or proportion of utterances of that category known to relate to average likelihood of improvement. In the example given in FIG. 13b, the mean number of 'change mechanisms' tagged utterances per session that correlates with average % improvement is 16-25, therefore a criterion may be predetermined that the desired minimum number of utterances of that category per therapy session is 16.

Where the selected utterance category relates to an utterance category known or suspected to correlate negatively with likelihood of patient recovery, the predetermined threshold or criterion is set at a desired maximum level (a predetermined maximum threshold), for example the maximum amount or proportion of utterances of that category known to relate to average likelihood of improvement.

Each session feature is compared with the predetermined threshold or criterion. Automated feedback is provided to the therapist on one or more session features. Where the predetermined threshold or criterion is a predetermined minimum threshold (i.e. where a session feature is a measure of an utterance semantic representation (category) that correlates positively with improved clinical outcome), if the session feature is below (does not meet) that level, the therapist is alerted. Where the predetermined threshold or criterion is a predetermined maximum threshold (i.e. where a session feature is a measure of an utterance semantic representation (category) that correlates negatively with improved clinical outcome), if the session feature is equal to or above (meets) that level, the therapist is alerted. Alternatively/additionally, automated feedback on the therapist's performance in relation to each or all of the session features may be provided to the therapist irrespective of whether the session feature is below or above a given predetermined threshold or criterion. Suitably, a therapist is provided with automated feedback on all session features available.

The automated feedback provided to the therapist may take the form of an alert. The automated feedback provided to the therapist may suitably take the form of a visual alert, for example a written (text) alert e.g. an automatically-generated email, a pop-up, a text-box or another form of message generated by the therapy system; alternatively/additionally, the visual alert may be for example a graphical alert e.g. a graphical pop-up, a bar chart, pie chart or line chart that e.g. compares the therapist's performance with the predetermined threshold or criterion. Other suitable alerts may be determined by reference to the particular interface used by the therapist. The alert provided to the therapist may automatically direct the therapist to take one or more actions e.g. suitably to recommend to either increase or decrease (in absolute number or frequency) the utterances belonging to one or more semantic representations, or one or more styles of communication. Alternatively the therapist may be automatically alerted that their performance appears to be of high quality as measured by the one or more metric or criterion, and they should maintain their current therapy delivery. In that way, the therapist is automatically alerted as to the quality of their performance.

For example, where the deep learning model determines in real-time that the likelihood of patient recovery is below average for a particular therapy session because the therapist is not delivering frequent enough utterances of the 'change mechanisms' type in a given unit time (for example 1, 2, 3, 4, 5, 6, 7, 8, 9, 10, 11, 12, 13, 14 or 15 minutes), the system will alert the therapist to the problem (the low likelihood of recovery and/or low frequency of utterances of that category) and automatically recommend that the therapist increases the frequency of utterances of that category. If the therapist responds by increasing the frequency of utterances of the 'change mechanisms' type delivered, the system will indicate that the frequency has increased and/or that the likelihood of recovery of the patient has increased. Therefore the therapist receives real-time feedback on the quality of therapy delivered and is prompted by the system as to how to improve the quality of the therapy.

Furthermore, the feedback provided to the therapist on the quality of the therapy delivered may take into account the characteristics of a particular therapy session. For example, by using the current therapy (e.g. CBT) clinical knowledge, session plans can be prepared automatically ahead of each session according to the patient's presenting condition and the chosen treatment model. The session may be monitored while in progress using the system or method, and the therapist may be alerted if the session appears to diverge from the recommended plan. The therapist may also get hints to help with e.g. time keeping, for example if less than 10 minutes of the session remain, but they have not yet started discussing homework for the next session. Therefore expected changes in utterance frequency during the course of a session may be taken into account.

Suitable recommendations that may be made to a therapist may include specific advice on session content, such as advice to not spend too much time on greetings and bridging, and an emphasis on setting a session agenda.

Automated Quality Assurance

An additional/alternative action that may be taken by the system at step S5 of the method is to perform automated quality assurance (QA) of therapy sessions. A supervisor may be alerted to below-average delivery of therapy by a therapist (e.g. a prediction of below average likelihood of recovery, based on the session features or representation of a therapy session). This alert may take the form of e.g. a quality score for a particular therapy session, based on the presence or absence of (or a certain amount or frequency of) expected utterance types. Supervisors may be alerted only where a session appears to diverge significantly from expected performance (i.e. where the therapy session meets a predetermined criterion). If the supervisor is thus alerted they may take one or more further action such as more closely monitoring the therapist, advising/supporting the therapist in making improvements, or re-allocating the patient to a different (more suitable) therapist where the therapist performance is particularly poor quality. The particular one or more action may be automatically recommended to the supervisor based on the representation of the therapy session meeting a certain predetermined criterion. For example, if the system detects that a therapist is otherwise performing well but is failing to use (enough of) a particular utterance category, the system may alert the supervisor that the likelihood of clinical improvement is below average (i.e. the quality of the therapy provided is low) and that the supervisor should recommend to the therapist that more/more frequent utterances of that type should be delivered. Thereby the system provides automated QA and therapy supervision support.

Alternatively/additionally, the method and system can be used to detect the amount of therapy being delivered in a particular therapy session. For example, if the session booked is 60 minutes long, but the therapist starts the session late or finishes it early, the patient may not receive the full time allocation of therapy, and therefore the 'dose' of therapy delivered may be less than that recommended. A therapist who consistently under-delivers therapy time could be awarded a lower quality score by the system.

The utterance assignment model is used to provide automated feedback on therapist performance to an entity other than the therapist, for example the therapist's supervisor, the therapist's employer, a therapy service, a healthcare provider or a health insurance company, in order that one or more appropriate actions or interventions may be taken by that entity. This can be considered a type of automated quality assurance. The automated quality assurance may be provided regarding one or more therapy sessions delivered by a particular therapist.

The automated quality assurance is provided either after a particular therapy session has been completed, or alternatively/additionally whilst the therapy session is still taking place (real-time or live automated quality assurance). The automated quality assurance may be provided for all therapy sessions delivered by a particular therapist to a particular patient, in order that changes in the quality of therapy delivered to that patient overtime can easily be identified, and one or more appropriate actions or interventions can be taken. Alternatively, the automated quality assurance may be provided for a subset of therapy sessions delivered by a therapist to a particular patient. This subset of therapy sessions may for example be chosen by the supervisor (e.g. the first and every alternate session), or may be randomly selected as part of the automated quality assurance. Alternatively, the automated quality assurance may be provided for a subset of all therapy sessions (e.g. a random sample of therapy sessions) provided by a particular therapist to all of their patients. Alternatively, all therapy session delivered by a particular therapist may be monitored by automated QA (analysis of a therapist's overall performance).

The automated QA may take into account the characteristics of a particular therapy session. For example, by using the current therapy (e.g. CBT) clinical knowledge, session plans can be prepared automatically ahead of each session according to the patient's presenting condition and the chosen treatment model. The session may be analysed using the system or method, and an alert may be generated if the session appears to diverge from the recommended plan.

The actions or interventions that may be taken by the entity (the therapist's supervisor, employer, therapy service, healthcare provider or health insurance company) in response to the automated quality assurance may include providing advice, support or education to the therapist in order that the therapist may improve the quality of the therapy provided, e.g. the identification of areas of potential improvement to be worked on during 1-1 supervision. For example a therapist may consistently be failing to check for risk, or only give out homework in a small fraction of sessions, or only give out generic and less helpful homework, such as psycho-education. Alternatively the action or intervention may include reallocating the patient to another therapist of greater experience or increased quality of therapy delivery. In these ways, the quality of care delivered to the patient is increased and therefore the likelihood of the patient improving or recovering is also increased.

By automating the QA, it is possible to provide QA on a greater number of therapy sessions at much reduced cost, thereby introducing the possibility of conducting QA on all therapy sessions. This is beneficial to patients (who are more likely to recover), therapists (who develop their professional expertise) and supervisors (who may therefore focus their expertise where it is most needed.)

Automated Auditing

An additional/alternative action that may be taken by the system at step S5 of the method is to initiate automated auditing of a therapy service. This involves the automatic collection of a plurality of outputs (output predictions) of the method and associated data relating to one or more therapy sessions/one or more therapists, in order that a therapy auditing process may be undertaken by e.g. a therapy service, a health insurance company, an employer, other payer of multiple instances of therapy, a health institution or a state or government body. The plurality of outputs may be anonymised with respect to the patients and/or the therapists. The automated audit may be used to compare e.g. therapy outcomes between different therapists or at different timepoints Automated Output Report An additional/alternative action that may be taken by the system at step S5 of the method is to initiate automated reporting of the output (prediction) of the method. The output report may be provided to the therapist, a supervisor of the therapist, a service to which the therapist belongs and/or the payer for the therapy for example an employer, health service or health insurer. The output of the method is a prediction of a characteristic of the therapist, the therapy, and/or the one or more patient, therefore following automated report of the output relating to one or more therapy session the therapist, the supervisor of the therapist, the service to which the therapist belongs and/or the payer for the therapy may take further actions appropriate to that prediction.

Automated Medical Diagnosis

An additional/alternative action that may be taken by the system at step S5 of the method is to provide automated medical diagnosis. The medical diagnosis relates to the one or more patient taking part in the therapy session. The medical diagnosis may be provided to the therapist, a supervisor of the therapist, a service to which the therapist belongs and/or the payer for the therapy for example an employer, health service or health insurer. The medical diagnosis comprises providing a prediction of the presence of a mental health disorder in the one or more patient, wholly or in part based on analysis of the patient utterances. Additional further actions may be taken by the system subsequent to provision of the medical diagnosis, such as recommendation of a particular therapy protocol to the therapist. In that way, the therapy delivered to the patient, and therefore the likely outcome for the patient, may be improved.

Automated Data Collection

An additional/alternative action that may be taken by the system at step S5 of the method is to perform automated data collection. This involves the automatic collection of data from any stage of the method including the audio data, the audio streams, the session transcript (text data), the utterances, the classified utterances, the optional additional inputs (non-content related session features and/or patient variables) and/or the representation. The data may be collected and stored by the system using any suitable method. The data collected can be used at a later stage to conduct research, further therapy product development, or kept for regulatory, quality assurance or auditing purposes.

Sixth Step of the Method

At a sixth step S6, the method ends.

EXAMPLES

It is beneficial to patients, therapists, therapy services and insurance companies to apply the additional benefits and improved outcomes of IECBT to face-to-face therapy sessions. The data relating to the therapy session, e.g. audio data (including speech data) from the spoken conversation between therapist and patient(s) in a face-to-face therapy session is acquired. This audio data is then analysed using similar methods/apparatus/system to the text transcript data obtained from IECBT to produce an output, and the method/apparatus/system takes the same or similar appropriate actions to improve patient outcome, provide therapist support or increase therapy service efficiency.

In Examples 1-5, the exemplary utterance assignment model used was an utterance classification model that assigned categories ('tags') to individual utterances in order to assign semantic representations.

Example 1

In this example, the one-to-one component of IECBT therapy sessions (i.e. patient-therapist interactions) was provided as text transcripts (text data). Within each transcript, individual parts of the text were automatically nominated as utterances, and were identified as originating from either the therapist or the patient, based on the individual text-based messages sent from either the therapist interface or the patient interface during the therapy session. Therefore the transcript of the therapy sessions was divided into therapist utterances and patient utterances, and also retained information regarding the relative positions of the utterances in the therapy session.

The next stage of the process was to design suitable semantic representations. In this example the semantic representations used were tags. A set of tags was designed to classify therapist and user/patient utterances. These tag-sets had to satisfy multiple requirements; they needed to:

Be unambiguous, such that multiple human annotators would agree in most cases how to classify a certain utterance;

Be simple, such that a reasonably sophisticated computer system would be able to automatically assign tags to utterances with a useful level of accuracy;

Be as complete as possible (within the bounds of the simplicity constraint), so as to maximise the amount of insights uncovered;

Include sufficient domain knowledge, such that useful insights can be derived from the tags associated with the utterances in a therapy session.

Following consultation between domain experts in clinical psychology and natural language processing, and multiple iterations of manual tagging exercises, the set of tags presented in Table 1 were arrived at. Other numbers and sets of tags may be determined to be suitable in other circumstances.

TABLE 1

Tag set/utterance types

Tags used for the content of therapist utterances (Therapist Utterance Categories)

1. Greeting
2. Mood check
3. Obtain update
4. Bridge from previous session
5. Review previous homework
6. Agenda setting
7. Implementing change mechanisms
8. Summarising session
9. Eliciting feedback
10. Setting homework
11. Risk check
12. Set goals
13. Discuss perceptions of change
14. Planning for the future
15. Formulation
16. Giving feedback
17. Arrange next session
18. Goodbyes
19. Other Tags used for the style of therapist communication (Therapist Communication Style)

20. Therapeutic alliance
21. Collaboration
22. Socratic questioning

Tags used for the content of user/patient utterances (User/Patient Utterance Categories)

23. Compliance
24. Non-compliance
25. Follow/neutral
26. Offer Information
27. Other Some of the categories are further exemplified in Table 2 below:

TABLE 2

Therapist utterance examples

| Therapist Utterance Category | Description | Example |
| --- | --- | --- |
| 1. Greeting | An initial greeting to welcome the patient to the session. | "Good morning . . . " |
| 5. Review previous homework | Reviewing and discussing patient's previous homework assignment. | "Did you manage to use that mood chart I sent you last week?" |
| 6. Agenda setting | Deciding and prioritizing the topic(s) to discuss during the therapy session. | "What issues shall we focus on today?" |
| 13. Discuss perceptions of change | Discuss what the patient feels they have learnt from therapy. | "What do you feel has helped you most during our time together?" |
| 15. Formulation | Framing patient's issues within the context of a CBT formulation. | "How do you think avoidance fits into the diagram we started in session 2?" |
| 17. Arrange next session | Arranging time and date of next appointment. | "Would you like to book another appointment for 10.00am next Thursday?" |

Once the tag sets were defined, the next stage was the production of a dataset comprising therapy session transcripts with all utterances manually tagged. In the first instance, as a feasibility test, a small number of therapy sessions were annotated in order to test the approach.

For comparison with previously available methods, regular expressions (regexes) were handcrafted to identify the 19 categories/tags used for the content of therapist utterances, and 3 categories/tags used for the style of therapist communication. Regexes are a simple approach for tagging natural language text, and have previously been used to categorize the utterances in the standard 60 minute therapy sessions available to date. Regexes are rules for identifying runs of text that satisfy specified structural constraints. Regexes are considered to be very precise (i.e. they do not make many false positive mistakes), but they suffer from low recall (i.e. they miss things, that is make false negative mistakes).

As an example, the 'Socratic Questioning' style of communication could be represented by a regex:

((what|why|how) do you think)(how (did|does) that make you)

Of the data from 97,263 sessions previously analysed, 69,342 utterances were found to match the above Socratic questioning regex.

A set of RegExes was produced for the classes of therapist utterance of interest, and used to estimate the feasibility of the proposed approach of correlating insights about the contents of therapy sessions and clinical outcomes. RegExes provided sufficient insight to identify some correlations, which provided the motivation to build more elaborate deep learning models for text tagging.

The utterance classification model developed uses recurrent neural networks (RNNs), with a two-level hierarchical structure: at the lower level, bi-directional RNNs are used to produce a representation of each utterance, while a higher level RNN is used to model each utterance in the context of the therapy session. The representation generated by the high level RNN was used as input to a multi-class multi-label classifier that emits likelihoods of each utterance belonging to each of the utterance classes present in the tag set.

Initial training of the deep learning utterance classification RNN model used 80 therapy session transcripts, while 20 were kept back for evaluating the accuracy of the model. The allocation of each utterance to a category by the model (to produce tagged utterances) was assessed using the F1 metric, which combines precision (positive predictive value) and recall (sensitivity) in a single number. Following initial training, as expected the deep learning model had significantly better recall than the RegEx system and the classification model already outperformed the regex approach (FIG. 9).

Example 2

For a subsequent expanded test using transcripts of 170 therapy sessions, only the therapist utterances (totaling 6698 individual utterances) were included.

The transcript data from 150 of the 170 hours of therapy sessions were used to train a deep learning utterance classification model, while the remaining 20 hour session transcripts were kept back for evaluating the accuracy of the model. The evaluation results are presented in FIG. 10, and indicate that the approach is feasible. The performance for each category was again measured using the F1 metric. As can be seen, even from a small amount of training data, many categories achieve F1 values of over 60%.

To confirm the results of the feasibility test, the overall F1 (macro-averaged) was also measured as a function of the number of session transcripts used as training data. As can be seen from FIGS. 11a and 11b, the accuracy of the utterance tagger continues to improve as more training data becomes available. Furthermore, the performance of the utterance classification model can again be seen to improve on the Regex approach (FIG. 11b). The improvement of the utterance classification model as a function of amount of training data suggests that, as expected, continual improvement of the model may be achieved by tagging the utterances from more therapy sessions.

Example 3

The resulting automatic utterance categorisation model was then used to tag a large number of therapy session transcripts (around 20,000). The relative frequency of each different therapist utterance type allocated by the model or a human annotator was plotted, as shown in FIG. 12. As can be seen, utterances in the 'change mechanisms' category, which constitute the active ingredient in cognitive behavioural therapy, made up the largest part of therapist utterances during the therapy sessions analysed using the model.

Example 4

As a further test, it was considered whether any features of the therapy sessions (session features, Table 3) and/or patient variables (Table 4) could be correlated with treatment outcome (% likelihood of patient recovery) for the data analysed for patients with known outcomes, and thereby be useful in prediction of recovery for future patients/users. Session features were categorised as 'non-content related' or 'content related' features (Table 3), where content-related features relate to tagged utterances, and the numbering of content related features matches that given for utterance categories in Table 1.

TABLE 3

Features of therapy sessions

| Non-content related features | Content related features E.g. Number, proportion or frequency of the following utterance categories: |
| --- | --- |
| Number of patient utterances | Greeting (1) |
| Number of therapist utterances | Mood check (2) |
| Number of patient words | Obtain update (3) |
| Number of therapist words | Bridge from previous session (4) |
| Number of patient characters | Review previous homework (5) |
| Number of therapist characters | Agenda setting (6) |
| Number of word types of patient | Implementing change mechanisms (7) |
| Number of word types of therapist | Summarizing session (8) |
| Number of turns taken in conversation | Eliciting feedback (9) |
| Time to first response for patient | Setting homework (10) |
| Time taken responding for patient (and therapist) | Risk check (11) |
| | Set goals (12) |
| Time of day of therapy session | Discuss perceptions of change (13) |
| Day of week of therapy | Planning for the future (14) |
| Duration of session | Formulation (15) |
| | Giving feedback (16) |
| | Arrange next session (17) |
| | Goodbyes (18) |
| | Therapeutic alliance (20) (e.g. "thanks for sharing") |
| | Collaboration (21) |
| | Socratic questioning (22) (e.g. "how does that make you") |

TABLE 4

Patient variables

| Patient variables | Input |
| --- | --- |
| Age of patient | Number of years |
| Gender of patient | M/F/Not known/Not disclosed |
| Starting PHQ score | 0-27 |
| Starting GAD score | 0-21 |
| Long-term health conditions | Y/N |
| Total number of therapy sessions completed by the patient | Number of sessions |

Using a logistic regression model of therapy outcome, certain content-related session features, non-content related session features and patient variables were found to positively correlate with patient recovery (Table 5). All transcripts for a single case (patient) were pooled and the average number of session features was obtained for that case. The values of each session feature were entered into a logistic regression with treatment outcome (whether the patient recovered) as a binary outcome.

Regarding content-related session features (relating to tagged utterances), both the absolute number, and the percentage of all utterances that were of a certain category, were modelled. The former produced stronger correlations for the utterance categories analysed.

TABLE 5

Session features/patient variables that showed a positive relationship with clinical improvement (utterance category/style numbering matches that in Table 1)

|  |  | Session features | Patient variables |
|---|---|---|---|
| Content-related | Therapist utterance categories | (7) '(Implementing) change mechanisms'*** <br> (13) 'Discussing perceptions of change'*** <br> (3) 'Obtain update'** <br> (6) 'Agenda setting'* <br> (9) 'Eliciting feedback'* <br> (18) 'Goodbyes'* | Age of patient*** <br> Total number of sessions*** <br> Start GAD score*** |
|  | Therapist communication style | (20) Therapeutic alliance*** <br> (22) Socratic questioning*** |  |
| Non-content-related |  | Number of sessions*** |  |

Significance:
***<0.001
**0.01
*<0.05
13,315 cases (engaged, at caseness, 2013-2018).

Therefore it can be seen that the presence of any one of 8 content-related session features (6 categories of therapist utterance, 2 therapist communication styles), one non-content related session feature, or 2 patient variables positively correlated with clinical improvement. The positive correlation between certain categories of therapist utterance and patient outcome is further quantified in FIG. 13a ('Agenda Setting'), FIG. 13b ('Change Mechanisms'), and FIG. 13c ('Eliciting Feedback') wherein in each case, increasing amounts of utterances of the given category correlate with a significant increase in the clinical improvement. In FIG. 13, the dashed horizontal line indicates the average improvement rate, i.e. the percentage of all cases that improve during treatment.

Positive correlations were also found between the therapist communication styles 'Therapeutic Alliance' and 'Socratic Questioning' and clinical improvement. It was also found that the total number of therapist utterances correlated positively with patient improvement.

Furthermore, using the same logistic regression model of therapy outcome, certain session features and patient variables were found to negatively correlate with clinical improvement (Table 6).

TABLE 6

Session features/patient variables that showed a negative relationship with improvement (utterance/style category numbering matches that in Table 1).

|  |  | Session features | Patient variables |
|---|---|---|---|
| Content-related | Therapist utterance categories | (11) Risk Check*** <br> (4) Bridge* <br> (21) Collaboration** | Long Term Conditions*** |
| Non-content related |  | Number of therapist utterances*** <br> Session duration*** |  |

Significance:
***<0.001
**0.01
*<0.05
13,315 cases (engaged, at caseness, 2013-2018).

Figure 13A:
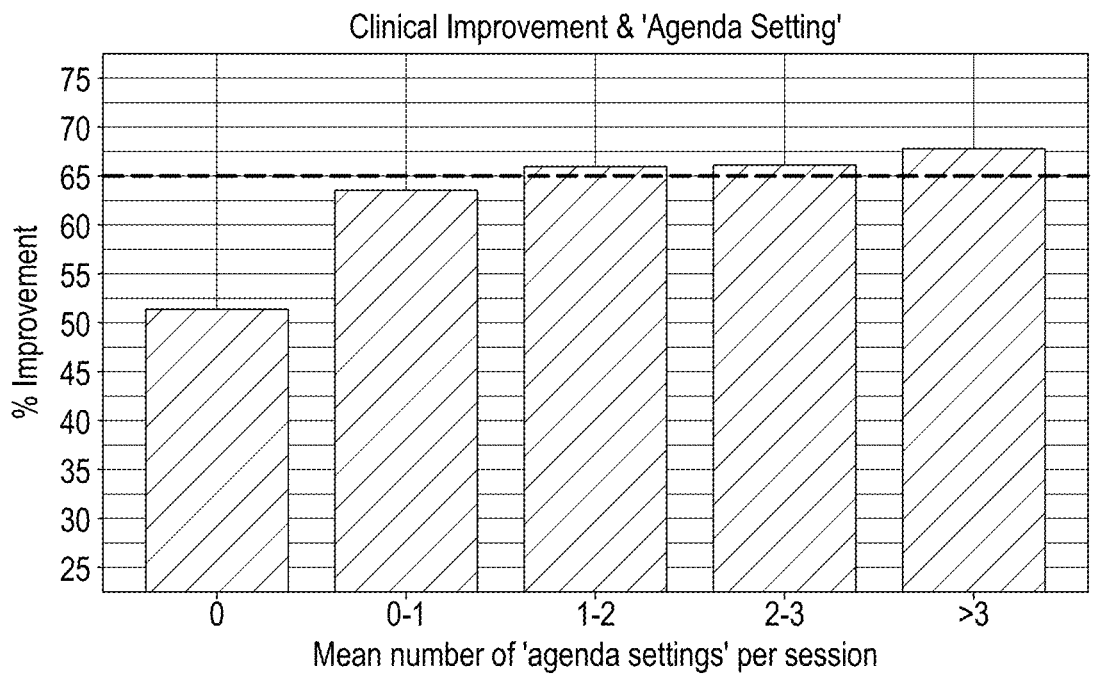
Figure 13B:
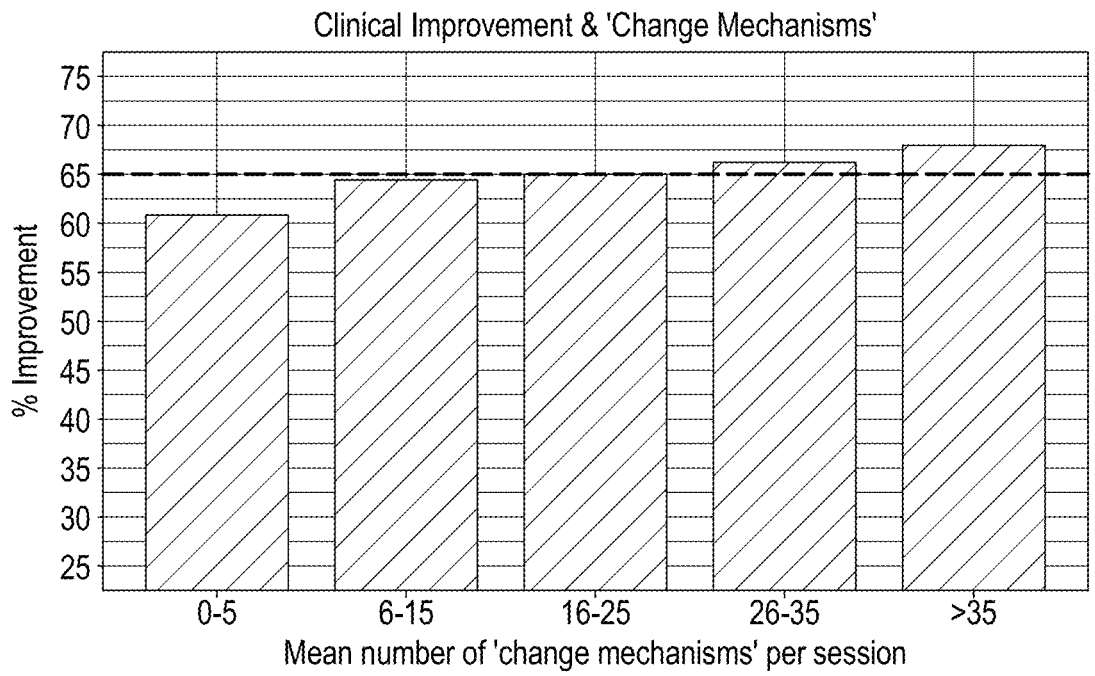
Figure 13C:
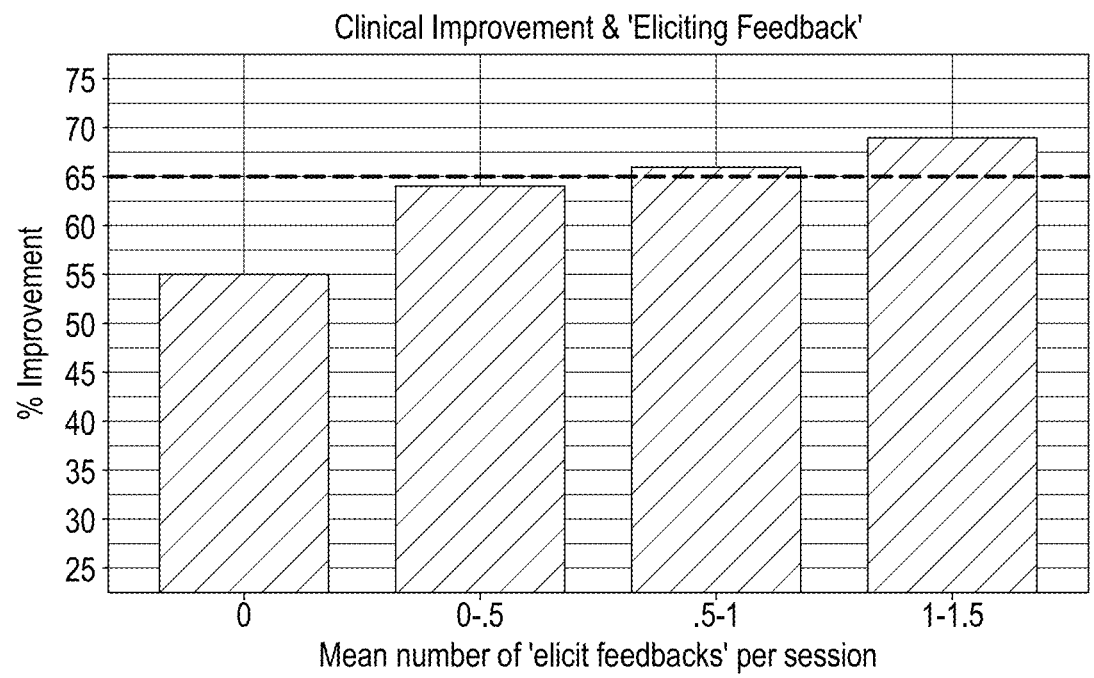
Figure 13D:
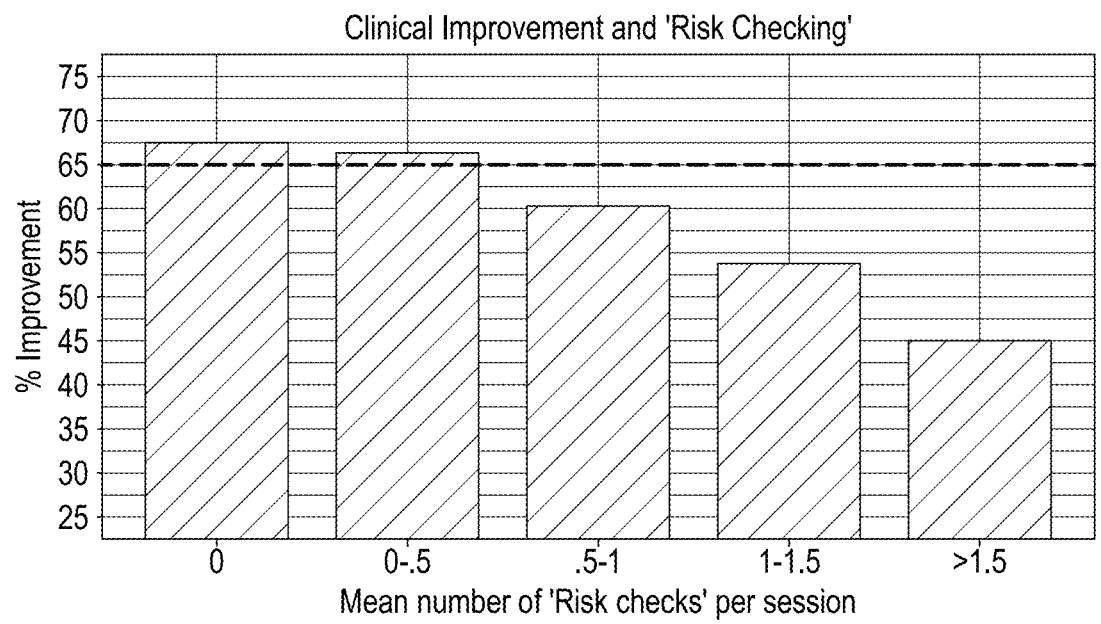

Therefore two content-related session features (both were therapist utterance categories) were identified that appear negatively correlated with clinical improvement (Table 6). As illustrated in FIG. 13d for the category 'Risk check', it can be seen that an increasing proportion of 'Risk check' utterances was associated with decreasing clinical improvement.

Example 5

Due to the large number of utterances that are categorised by the model as belonging to the category 7 'Implementing change mechanisms', and in order to gain even deeper insights into the therapy process, the tagging/categorisation schema has been refined by defining a hierarchy of sub-categories within that category. Two extra levels of sub-hierarchy are shown in Table. Category 7 has been divided into 5 first level sub-categories (7.1-7.5), each of which has then been further sub-divided.

TABLE 7

Further levels of 'Implementing change mechanisms' categorisation 7.1 Cognitive reattribution 7.1.1. Worry thought record
7.1.2. Suppression experiments
7.1.3. Challenging meta-worry
7.1.4. Questioning the evidence
7.1.5. Questioning the mechanism
7.1.6. Questioning uncontrollability
7.1.7. Enhancing cognitive dissonance
7.1.8. Controlled worry periods
7.1.9. Cognitive restructuring (diary/thought record)
7.1.10. Cognitive restructuring (guided imagery)
7.1.11. Re-evaluation of positive beliefs about worries
7.1.12. Learning to let go of worries
7.1.13. Guided discovery
7.1.14. Elicit, record and manage negative automatic thoughts
7.1.15. Elicit values/or core beliefs
7.1.16. Identify beliefs and misinterpretations
7.1.17. Behavioural experiments
7.1.18. Surveys
7.1.19. Updating trauma memory
7.1.20. Impact statement
7.1.21. Identification of meaning and stuck points
7.1.22. Reliving
7.1.23. Identifying hot spots and meanings
7.1.24. Using feedback
7.1.25. Rescripting early memories
7.1.26. Manipulation of self-focussed attention and safety behaviours
7.1.27. Attention training
7.1.28. Controlled worry periods
7.1.29. Learning to let go of worries
7.1.30. Suppression experiments
7.1.31. Cost benefit analysis 7.2. Behavioural reattribution 7.2.1. Exposure
7.2.2. Worry behaviours
7.2.3. Activity scheduling
7.2.4. Functional analysis
7.2.5. Action plans
7.2.6. Identifying safety behaviour
7.2.7. Explore avoidance
7.2.8. Revisiting site of trauma
7.2.9. Graded hierarchy 7.3. Conceptualisation 7.3.1. Recognising pleasant outcomes from uncertain situations
7.3.2. Cross sectional, longitudinal or disorder specific formulation
7.3.3. Establish links between physical symptoms and thoughts emotions and behaviours 7.4. Skill Teaching 7.4.1. Relaxation
7.4.2. Problem solving training
7.4.3. Breathing retraining TABLE 7-continued Further levels of 'Implementing change mechanisms' categorisation 7.4.4. Progressive muscular relaxation training
7.4.5. Synthesizing learning
7.4.6. Guided self-dialogue
7.4.7. Reclaiming your life
7.4.8. Ritual prevention
7.4.9. Mindfulness
7.5. Psychoeducation 7.5.1. Normalizing
7.5.2. Synthesizing and consolidating learning
7.5.3. Psychophysiology
7.5.4. Socialise to the CBT model
7.5.5. General information
7.5.6. Treatment rationalization
7.5.7. Synthesizing and consolidating learning The sub-categories are used to re-tag the therapy session transcripts and retrain the RNN model (HiBiLSTM therapy insights model), in order to provide more detailed information on the key aspects of good (high quality) therapy and improve the precision of the methods of the invention. By using the deep learning model (HiBiLSTM therapy insights model) to perform large-scale analysis of therapy sessions and sub-classify certain categories of utterance e.g. 'change mechanisms', it is possible to identify which particular change mechanisms are most effective. By performing the analysis on therapy data relating to a particular group of patients, it is possible to identify which particular change mechanisms work best for those patients, e.g. young female patients presenting with anxiety, or older males presenting with depression and a co-morbid long term physical condition. Based on this insight, more personalised treatment plans are automatically produced for each patient. For example, whichever of the possible change mechanisms should be used for each patient is recommended, by optimising for various clinical measures such as likelihood of recovery, likelihood of improvement, or engagement.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described byway of example with reference to several embodiments. It is not limited to the disclosed embodiments and that alternative embodiments could be constructed without departing from the scope of the invention as defined in the appended claims.

The term "comprising" encompasses "including" as well as "consisting" e.g. a composition "comprising" X may consist exclusively of X or may include something additional e.g. X+Y.

The terms "about" or "approximately" in relation to a numerical value x is optional and means, for example, x±10%.

The invention claimed is:

1. A computer-implemented method for performing real-time therapy improvements, the therapy comprising psychotherapy or cognitive behavioral therapy for one or more patients with a mental health disorder, the method comprising:
obtaining, at a computing system, data comprising audio data relating to a therapy session between a therapist and the patients;
extracting, via the computing system, text data from the audio data to form a transcript;
dividing, via the computing system, the transcript into a plurality of utterances;
using, at the computing system, at least a first part of a deep learning model to assign a semantic representation to each of the plurality of utterances to produce a plurality of assigned utterances;
compiling, via the computing system, the plurality of assigned utterances to form a representation of the therapy session;
using, at the computing system, at least a second part of a deep learning model, and an input comprising the representation of the therapy session, to obtain an output predicting a characteristic of the therapist, and/or the therapy, and/or the one or more patients;
outputting, in real-time during the therapy session and from the computing system, an alert comprising feedback to a therapist of the therapy session, the feedback recommending one or more actions based at least in part on the output, wherein the feedback is determined to improve the therapy for the one or more patients with the mental health disorder,
wherein the one or more actions comprises adjusting via an increase or a decrease of a frequency of utterances belonging to each of a plurality of categories determined to affect a therapeutic quality of the therapy, wherein the frequency of utterances for each category is adjusted to an improved therapeutic amount determined based at least in part on the output and corresponding to the therapy; and
taking the one or more actions relating to the therapy, and wherein the one or more actions relating to the therapy are taken in real-time whilst the therapy session is ongoing.

2. A method according to claim 1, wherein the audio data is separated into two or more audio streams by speaker diarization, each audio stream relating to one of the therapist or the one or more patients.

3. A method according to claim 1, wherein each of the plurality of utterances is ascribed to either the therapist or the one or more patients to produce a plurality of therapist utterances and a plurality of patient utterances.

4. A method according to claim 1, wherein obtaining the audio data comprises capturing the audio data in real-time during the therapy session via a microphone array.

5. A method according to claim 1, wherein the data further comprises video and/or passive data from the therapy session.

6. A method according to claim 1, wherein the assigned utterances comprise tagged utterances.

7. A method according to claim 1, wherein the input further comprises non-content related session features and/or patient variables.

8. A method according to claim 1, wherein the deep learning model comprises a bidirectional long short-term memory (BiLSTM) neural network or a hierarchical bidirectional long short-term memory (HiBiLSTM) neural network.

9. A method according to claim 1, wherein the output or outputs comprise:
- a likelihood of clinical improvement by the patient; and/or
- a likelihood of clinical recovery by the patient; and/or
- a likelihood of the patient having a particular mental health disorder; and/or
- a likelihood of engagement by the patient; and/or
- a measure of quality of therapy delivered by the therapist.

10. A method according to claim 1, wherein the output or outputs are generated in real-time whilst the therapy session is ongoing.

11. A method according to claim 1, wherein the one or more actions comprise:
- initiating an automated therapist support process that comprises providing information to the therapist; and/or
- initiating an automated therapy auditing process that comprises collecting a plurality of outputs of the method relating to one or more therapy sessions or one or more therapists; and/or
- initiating an automated output report to one or more of: the therapist, a supervisor of the therapist, a service to which the therapist belongs and the payer for the therapy; and/or
- initiating an automated medical diagnosis process that comprises providing a prediction of the presence of a mental health disorder in the one or more patient; and/or
- initiating an automated data collection process that comprises storing the audio data, an audio stream of the audio data, the transcript, the utterances, the assigned utterances, and/or the representation.

12. A method according to claim 11, wherein the audio data, and/or the audio streams, and/or the transcript are provided to one or more of: the patient, the therapist, the supervisor of the therapist, the service to which the therapist belongs and the payer for the therapy.

13. The method according to claim 1, further comprising:
receiving, via at least one video input device, real-time video data associated with the therapy session, wherein the deep learning model is configured to perform the first part, the second part, or both the first part and the second part based at least in part on the video input device.

14. The method according to claim 1, further comprising:
detecting the output indicates performance of a poor therapy delivery during the therapy session; and
outputting a second alert to a supervisor interface, wherein the second alert indicates at least the performance of the poor therapy delivery during the therapy session.

15. The method according to claim 1, wherein outputting in real-time during the therapy session, the alert comprises: causing rendering of the alert to a therapist interface viewed by the therapist during the therapy session.

16. A method according to claim 1 where the mental health disorder is selected from depression or an anxiety disorder.

17. A system for carrying out the method according to claim 1, the system comprising: a processor; a natural language processing unit; and a memory unit.

18. A non-transitory computer-readable medium comprising instructions which, when executed by a processor, cause the processor to carry out the method of claim 1.

* * * * *